US011261498B2

(12) United States Patent
Januario et al.

(10) Patent No.: US 11,261,498 B2
(45) Date of Patent: Mar. 1, 2022

(54) METHODS FOR DIAGNOSING AND TREATING CANCER

(71) Applicant: Genentech, Inc., South San Francisco, CA (US)

(72) Inventors: Thomas E. Januario, San Francisco, CA (US); David Shames, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/591,253

(22) Filed: Oct. 2, 2019

(65) Prior Publication Data
US 2020/0024670 A1  Jan. 23, 2020

Related U.S. Application Data

(63) Continuation of application No. 15/638,135, filed on Jun. 29, 2017, now abandoned, which is a continuation of application No. 14/551,528, filed on Nov. 24, 2014, now abandoned, which is a continuation of application No. 13/599,611, filed on Aug. 30, 2012, now abandoned.

(60) Provisional application No. 61/529,917, filed on Aug. 31, 2011.

(51) Int. Cl.
*C12Q 1/6886* (2018.01)
*A61K 31/517* (2006.01)

(52) U.S. Cl.
CPC .......... *C12Q 1/6886* (2013.01); *A61K 31/517* (2013.01); *C12Q 2600/106* (2013.01); *C12Q 2600/154* (2013.01); *C12Q 2600/156* (2013.01)

(58) Field of Classification Search
CPC ............ C12Q 1/6886; C12Q 2600/106; C12Q 2600/154
See application file for complete search history.

(56) References Cited

U.S. PATENT DOCUMENTS

| | | | |
|---|---|---|---|
| 2004/0132097 A1 | 7/2004 | Bacus et al. |
| 2005/0019785 A1 | 1/2005 | Baker et al. |
| 2005/0202490 A1 | 9/2005 | Makarov et al. |
| 2007/0020261 A1 | 1/2007 | Sliwkowski et al. |
| 2007/0054295 A1 | 3/2007 | Spivack et al. |

FOREIGN PATENT DOCUMENTS

| | | |
|---|---|---|
| EP | 1 114 860 A1 | 7/2001 |
| WO | 2004/063709 A2 | 7/2004 |
| WO | 2004/071572 A2 | 8/2004 |
| WO | 2004/111273 A2 | 12/2004 |
| WO | 2004/111273 A3 | 12/2004 |
| WO | 2005/017493 A2 | 2/2005 |
| WO | 2006/101925 A2 | 9/2006 |
| WO | 2011/051414 | 10/2010 |

OTHER PUBLICATIONS

Agrawal et al., "Overview of tyrosine kinase inhibitors in clinical breast cancer" Endocrine-Related Cancer 12(2005):S135-S144 ( 2005).
Balko et al., "Gene expression patterns that predict sensitivity to epidermal growth factor receptor tyrosine kinase inhibitors in lung cancer cell lines and human lung tumors" BMC Genomics 7:289 ( 2006).
Bates et al., "Flt-1-dependent survival characterizes the epithelial-mesenchymal transition of colonic organoids" Curr Biol. 13(19):1721-7 ( 2003).
Baylin et al., "A decade of exploring the cancer epigenome—biological and translational implications" Nat Rev Cancer 11(10):726-34 ( 2011).
Belinsky et al., "Promoter hypermethylation of multiple genes in sputum precedes lung cancer incidence in a high-risk cohort" Cancer Res. 66(6):3338-44 ( 2006).
Benjamini and Hochberg, "Controlling the false discovery rate: a practical and powerful testing" J Royal Statist Soc B 57(1):289-300 ( 1995).
Brock et al., "DNA methylation markers and early recurrence in stage I lung cancer" N Engl J Med. 358(11):1118-28 ( 2008).
Davidson et al., "Of Snail, mice, and women" Cancer Cell 8(3):173-4 ( 2005).
Dermer et al., "Another anniversary for the war on cancer" Bio/Technol 12:320 ( 1994).
Dragovich et al., "Phase II Trial of Erlotinib in Gastroesophageal Junction and Gastric Adenocarcinomas: SWOG 0127" J Clin Oncol ((ERRATA p. 2334)), 24(30):4922-4927 (Oct. 20, 2006).
Du et al., "Comparison of Beta-value and M-value methods for quantifying methylation levels by microarrays analysis" BMC Bioinformatics 11:587 ( 2010).
Du et al., "lumi: a pipeline for processing Illumina microaray" Bioinformatics 24(13):1547-8 ( 2008).
Dumont et al., "Sustained induction of epithelial to mesenchynal transition activates DNA methylation of genes slienced in basal-like breast cancers" Proc Natl Acad Sci U S A. 105(39):14867-72 ( 2008).
Fang et al., "Breast cancer methylomes establish an epigenomic foundation for metastasis" Sci Transl Med. 3(75):75ra25 ( 2011).
Feinberg et al., "Hypomethylation distingushes genes of some human cancers from their normal counterparts" Nature 301:89-92 ( 1983).
Feng et al., "DNA hypermethylation, Her-2/neu overexpression and p53 mutations in ovarian carcinoma" Gynecol Oncol. 111(2):320-9 ( 2008).

(Continued)

Primary Examiner — Joseph G. Dauner
(74) Attorney, Agent, or Firm — Rahul Vartak

(57) ABSTRACT

The present invention provides methods of treating cancer based on the methylation status of the ERBB2 gene. One aspect of the invention provides a method of administering an EGFR inhibitor therapy based on the methylation status of the ERBB2 gene.

12 Claims, 8 Drawing Sheets
Specification includes a Sequence Listing.

(56) References Cited

OTHER PUBLICATIONS

Grille et al., "The protein kinase Akt induces epithelial mesenchymal transition and promotes enhanced motility and invasiveness of squamous cell carcinoma lines" Cancer Res. 63(9):2172-8 ( 2003).
Hanahan et al., "Hallmarks of cancer: the next generation" Cell 44(5):646-74 ( 2011).
Hattori et al., "DNA demethylase is expressed in ovarian cancers and the expression correlates with demethylation of CpG sites in the promoter region of c-erbB-2 and survivin genes" Cancer Letters 169:155-164 ( 2001).
Herbst et al., "Lung cancer" N Engl J Med. 359(13):1367-80 ( 2008).
Hirsch et al., "Predictive value of EGFR and HER2 overexpression in advanced non-small-cell lung cancer" Oncogene 28( SUPPL 1):S32-7 ( 2009).
Hoeflich et al., "In vivo Antitumor Activity of MEK and Phosphatidylinositol 3-Kinase Inhibitors in Basal-Like Breast Cancer Models" Clin Cancer Res 15(14):4649-4664 (Jul. 15, 2009).
International Search Report for PCT. App. No. PCT/US2012/053114, dated Nov. 20, 2012, 5 pages.
Ishii et al., "Characterization of the promoter region of the human c-erbB-2 protooncogene" Proc. Natl. Acad. Sci. 84:4374-4378 (Jul. 1987).
Jemal et al., "Cancer statistics, 2010" CA Cancer J Clin. 60(5):277-300 ( 2010).
Kalluri et al., "The basics of epithelial-mesenchymal transition" J Clin Invest. 119(6):1420-8 ( 2009).
Kang et al., "Epithelial-mesenchymal transitions: twist in development and metastasis" Cell 118(3):277-9 ( 2004).
Lu et al., "Downregulation of caveolin-1 function by EGF leads to the loss of E-cadherin, increased transcriptional activity of beta-catenin, and enhanced tumor cell invasion" Cancer Cell 4(6):499-515 ( 2003).
Mani et al., "The epithelial-mesenchymal transition generates cells with properties of stem cells" Cell 133(4):704-15 ( 2008).
McDonald et al., "Genome-scale epigenetic reprogramming during epithelial-to-mesenchymal transition" Nat Struct Mol Biol. 18(8):867-74 ( 2011).
Moulder et al., "Epidermal growth factor receptor (HER1) tyrosine kinase inhibitor ZD1839 (Iressa) inhibits HER2/neu (erbB2)-overexpressing breast cancer cells in vitro and in vivo" Cancer Res 61(24):8887-8895 (Dec. 15, 2001).
Neve et al., "A collection of breast cancer cell lines for the study of functionally distinct cancer subtypes" Cancer Cell 10(6):515-27 ( 2006).
Noushmehr et al., "Identification of a CpG island methylator phenotype that defines a distinct subgroup of glioma" Cancer Cell 17(5):510-22 ( 2010).
O'Byrne et al., "Molecular biomarkers in non-small-cell lung cancer: a retrospective analysis of data from the phase 3 FLEX tudy" Lancet Oncol. (study), 12(8):795-805 ( 2011).
Pao et al., "Rational, biologically based treatment of EGFR-mutant non-small-cell lung cancer" Nat Rev Cancer 10(11):760-74 ( 2010).
Patel et al., "Neuregulin-1 and human epidermal growth factor receptors 2 and 3 play a role in human lung development in vitro" Am J Respir Cell Mol Biol. 22(4):432-440 ( 2000).
Ramirez et al., "Immortalization of human bronchial epithelial cells in the absense of viral oncoproteins" Cancer Res. 64(24):9027-34 ( 2004).
Rothenberg et al., "Randomized Phase II Trial of the Clinical and Biological Effects of Two Dose Levels of Gefitinib in Patients With Recurent Colorectal Adenocarcinoma" J Clin Oncol 23(36):9265-9274 (Dec. 20, 2005).
Sato et al., "A translational view of the molecular pathogenesis of lung cancer" J Thorac Oncol. 2(4):327-43 ( 2007).
Sato et al., "Multiple oncogenic changes (K-RAS(V12), p53 knockdown, mutant EGFRs, p16 bypass, telomerase) are not sufficient to confer a full malignant phenotype on human bronchial epithelial cells" Cancer Res. 66(4):2116-28 ( 2006).
Savagner, "Leaving the neighborhood: molecular mechanisms involved during epithelial-mesenchymal transition" Bioessays 23(10):912-23 ( 2001).
Sequist et al., "Genotypic and histological evolution of lung cancers acquiring resistance to EGFR inhibitors" Sci Transl Med. 3(75):75ra26 ( 2011).
Shames et al., "A genome-wide screen for promoter methylation in lung cancer identifies novel methylation markers for multiple malignancies" PLos Med. 3(12):e486 ( 2006).
Sharma et al., "A chromatin-mediated reversible drug-tolerant state in cancer cell subpopulations" Cell 141(1):69-80 ( 2010).
Shepherd et al., "Erlotinib in previously treated non-small-cell lung cancer" N Engl J Med. 353(2):123-32 ( 2005).
Shivapurkar et al., "Application of a methylation gene panel by quantitative PCR for lung cancers" Cancer Lett. 247(1):56-71 ( 2007).
Singh et al., "A gene expression signature associated with 'K-Ras addiction' reveals regulators of EMT and tumor cell survival" Cancer Cell 15(6):489-500 ( 2009).
Singh et al., "EMT, cancer stem cells and drug resistance: an emerging axis of evil in the war on cancer" Oncogene 29:4741-5751 ( 2010).
Stinson et al., "miR-221/222 targeting of trichorhinophalangeal 1 (TRPS1) promotes epithelial-to-mesenchymal transition in breast cancer" Sci Signal 4(1986):pt5 ( 2011).
Stinson et al., "TRPS1 targeting by miR-221/222 promotes the epithelial-to-mesenchymal transition in breast cancer" Sci Signal 4(177):ra41 ( 2011).
Suda et al., "Epithelial to mesenchymal transition in an epidermal growth factor receptor-mutant lung cancer cell line with acquired resistance to erlotinib" J Thorac Oncol. 6(7):1152-61 ( 2011).
Tan et al., "Variable promoter region CpG island methylation of the putative tumor suppressor in breast cancer" Carcinogenesis 23(2):231-236 (Feb. 23, 2002).
Thiery et al., "Epithelial-mesenchymal transitions in tumour progression" Nat Rev Cancer 2(6):442-54 ( 2002).
Travis et al., "International association for the study of lung cancer/american thoracic society/european respiratory society international multidisciplinary classification of lung adenocarcinoma" J Thorac Oncol. 6(2):244-85 ( 2011).
Tryndyak et al., "E-cadherin transcriptional down-regulation by epigenetic and microRNA-200 family alterations is related to mesenchymal and drug-resistant phenotypes in human breast cancer cells" Int J Cancer. 126(11):2575-83 ( 2010).
Vaissiere et al., "Quantitative Analysis of DNA Methylation Profiles in Lung Cancer Identifies Aberrant DNA Methylation of Specific Genes and Its Association with Gender and Cancer Risk Factors" Cancer Research 69(1):243-252 (Jan. 1, 2009).
Walter et al., "DNA methylation profiling defines clinically relevant biological subsets of non-small cell lung cancer" Clin Cancer Res. 18(8):2360-73 ( 2012).
Warzecha et al., "An ESRP-regulated splicing programme is abrogated during the epithelial-mesenchymal transition" EMBO J. 29(19):3286-300 ( 2010).
Werth et al., "The transcription factor grainyhead-like 2 regulates the molecular composition of the epithelial apical junctional complex" Development 137(22):3835-45 ( 2010).
Wiklund et al., "Coordinated epigenetic repression of the miR-200 family and miR-205 in invasive bladder cancer" Int J Cancer 128(6):1327-34 ( 2011).
Wu et al., "Comparison of gefitinib and erlotinib in advanced NSCLC and the effect of EGFR mutations" Lung Cancer 72(2):205-12 ( 2011).
Yamamoto et al., "Impact of EGFR mutation analysis in non-small cell lung cancer" Lung Cancer 63(3):315-21 ( 2009).
Yauch et al., "Epithelial versus mesenchymal phenotype determines in vitro sensitivity and predicts clinical activity of erlotinib in lung cancer patients" Clin Cancer Res 11:8686-8698 ( 2005).

GCCAACCCAGCCCAGCCACCCTGCCCTCCGTAGAGCCTGTCTGGTGTGTTTATGGTGGCATTGGGAGTGGCATTAGTGTGTATTTATGTTGGCGTG
GGGTGTGGGGTGGATTTGTGTGTGTGAGGCGAGAGTAAGGCCTAGTTGCAGTTGGAAGGAATGTGGAGATCTGAAGGCAGGCCAGCTGAGTTCCAGTCCTGC
CTGTTGCTCACAAGCTTTATGAGGCGAGAGTAAGCTAACCCTGCCAGCTCAGTTGTCTTCTTTGCAAGATGGAGGTTGCAGCCCCAGTCTCTG
AGCATGTTATGCAGATCCACCAGGGCTGCCTGCCAGGCACACAGTAGGTGCTCAGTCAGTTACTGTGGGGACCCTGCCCAGCCCTGTGGAG
GTTGTTTCCTATTGCCTGGCCAGGGCCTGGGGTCTGGCCTGCCACCCCAGTCCTGCCAGAGACAGCTGTGTCTGTTCTCTGGGAGTCTGTTGGGAGGGCTGAGGGCTGAGGGGAGTCC
ACCTGGGCTTGGGCCAGAGGCCGGTTATTTGGGGTCTGGCCACCCCCAGTCCTCCTGCCTGCCCAGGCTGTGTCAGAGACAGCTGTGTCTGTTCTCTGGGAGTCTGTTGGGAGTCC
TGGCAGCAGGGCGGGTTATTTGGGGTCTGGCCACCCCCAGTCCTCCTGCCTGCCCAGGCTGTGTCAGAGACAGCTGTGTCTGTTCTCTGGGAGTCTGTTGGGGAGGAAGTGTGGGAAGAG
GAGGGGTGCAAGTGGGTGAGGGATGGGAGTGGGGAGGCATGGGAGTGGGAGGCATGGAGTCTATTTCTGTTCCTCCTGTT
CCTCCCTCTTTGTCCTTATCTGCCTAGAGAGTGGAATAGAGCCCATTCTGAGTATCACTAGAGACCACCAGTTTGTGGCCACTGGCCA
CTGGCCCAGGCAGGAACCTGGGGGCTTGCCCCTACCAGCCTCTGGTGTCCCAGCAATCTGAAGGCAGGGGTACCTCGTATTACCCCTCCTAGGATT
TGACCTTAGGCTCCAACTGCTGTGGAGAGCAGTGCCTCTGGTGTCAGTCAGGAATTCTGGGAGGCTGAGGGCCTGTGCTGTCCCTGAATCTGCATGTAGCC
TGTGGGAGGCGGAGCAGTGACCGGCAGGAATTCTGGGAGGCACTTTAATCTCCCTCATTCCTAGTGGGCATTTCTGGTCTCAGGAT
CTCCTGGGCAGCAAGACACGCCAGTGTGATTCATCTCACCAGGGTGCTTACCCCTATGCCCCAGTGCAGAGCCTGGGTCGAGCTTAGCTGGCGCCAGCTGGAGCATGCAGGGCTG
GGTGTGAGCTGCTACCCCGCCAGGGTGCTTACCCTATGCCCATGCCCATGCCCGCTGATGCTGCGCTGGGCGCTGGGCTGATGCAGGGCTG
ACCAGGCTGGGGTGCAAGTGGGCCAGTGGGCAGTTCAGCCCATGGGGCTGGCCATGGGCAGTTCAGCCCATGGGGCTGGCCATGGGCTGGGAGAGGTGGCCAGTGGCCAGGTGAGGGT
ACGTAGTGCCTTGTGCAGCAGTTCGTGCACACTCTGCCTGGTCTGCCCAGCTGGTCTGGGCACAGTTCGGGCAGTTCTGCAGGCATGGCACCCTCTGTCTCGCCATGCTCGCCATGCTCGCCAGGGACCTCCTGAGGCTGGCCAGGGTGGCCAGGGTGAGGGT
GCCAGGGCAGGAACCTTTGGGCGCATGTTCACCCTGGGACTCCCAGAGGTCTGCAATGACACCAGACCCAGCCCAAGAGTTCAGCCTGCAACTCCAGCTGCAACTCAGCCTGCTCCTGACCCTGCAACTCGACGCTCCTTCC
TCCTCATGGGACTCCCAGAGGTCTGCAATGACACCAGACCCAGCCCAAGAGTTCAGCCTGCAACTCCAGCTGCAACTGGCATAGGAGAATGCACC
CCACTCTCGGGTGGCATTACGGGGAGGGGCAGGGGGCAGGGGTATCCAGAAGATTCATGATTCGTCATCGCGCCCCTGTCCTCTTGGGGATTTTTACCCCTTTGCCCT
GAGTTGTTTGCTTTGGGACAAGGAAGCCTTTCTTTGCCAGCCAACACCCTGTCAGGCTTCCCCATCTGTCCTCTGACCCTCCCGCCCAGGGCTGCCCAGGGCTGCCAGGGCTGCCAGGGCTGCCAGCTGCAACCTGACCCCCTTCCCAGCCAACACCCTGTCAGGCTTCCCCATCTGTCCTCTGACCCTCCCGCCCAGGGCTGCCAGCCGCTCCCAGGCGCTGCCAGCCAGCAACGCTGGACGCTGGCAC
GAGTTGTGCCTTGGACAAGGAAGCCTTCTTGCCAGCCAACACCCTGTCAGGCTTCCCCATCTGTCCTCTGACCCTCCCGCCCAGGGCTGCCAGCCGCTCCCAGCCGCTGGACGGGC
AGCCTCTGAATGCACAGGGTGGGCCTAGTGGGCCTAGTGGGCCTAGTGCGAGAAGAAGCCCTTACTCTGAAATCCCTGAAATCCCTGTCCCTCAGTCAGGGGCTTCCCAGCACGCAAGCTTCTCTGCTGTT
AAACCTGCAGTGTGCAAGTGGCAGTCAGGTGGCCCTGGAAGGTGGCCCTGGAAGGTCCCTGTGTCTGAGAAGTCCCCGGCCAGTGTCCCAGCTGGGCAGGCATGGCATGACTTGGAGTGAGTTGG
ATGGGGTGCCAGGTCTGAAGAGTGCCCGGACAACCTGAGAAGGTCCCGGAGACCCTGAGAACCGGAGACCCTGAGAAGCCTGCAACATGAAG
CTGCGGCTCCCCTGGCCAGACCACCCTGAGAAGGTCCCGGAGACCCTGAGAACCGAGAAGGGCTGCCAGGTGGCTGCCAGGTGGCTGCAGGGTGCAGGAAACCTGGAACTC
ACCTACCTGGCCACCAATGCACCCCACCAATGCCACCACCGGTCCTTCCTGCAGGTGAGGCCCCTCTCGTTTCCTCCCGTCCCGGCCCCGCCCCGCGCCCTGTGTCCTCCTGCCAGCCTCCGCAGGTGAGGCCTGCAGGTGAGGCCTGCAGGTGAGGCCCTGCAGGTGAGGCCCTGCAGGTGAGGCCCTGCAGGTGAGGGCCGCTGAGCC
CTCTGTTTACAGGTGGTGGCCAGAAGAAGGTGCCCCCTTCGTGTCCCCCTCTGTTTCCTCCTCTGTTTCCTCCTCTGTTTCCTCCTCTGTTTCCTCCTCTGTGTCCAGTGCAGTAGTTCGATCCTCCTTCCTGTGGTGCCCCTGCAGTCGCCAGTCAGCCGTCATGGAAGGGCAAGGACCAGGGCCAGGGCAAGGGCTTCTCTGTCTTGTTGTGTCCAGGAAGTCCTTTCTAACAT
CTAACCCCATTCATTTTACTGACTCTCTATAACGTGACTGTCTGAGGTCATGTCTGAGGGATGGGATGGAGGATGGCTGTCTGTGCTGGATGCTGGATGCTGGATGGCTGGATGCTGGTTTC
CGCTAAATCTTGTGCTCTCTT (SEQ ID NO: 1)

*FIG. 1*

METHODS FOR DIAGNOSING AND TREATING CANCER

CROSS REFERENCE TO RELATED APPLICATIONS

This application is a Continuation of U.S. application Ser. No. 15/638,135, filed Jun. 29, 2017, which is a Continuation of U.S. application Ser. No. 14/551,528, filed Nov. 24, 2014, which is a Continuation of U.S. application Ser. No. 13/599,611, filed Aug. 30, 2012, which claims the benefit of U.S. Provisional Application No. 61/529,917, filed Aug. 31, 2011, the disclosures of which are incorporated herein by reference in its entirety.

SEQUENCE LISTING

The present application contains a Sequence Listing which has been submitted in ASCII format via EFS-Web and is hereby incorporated by reference in its entirety. Said ASCII copy, created on Aug. 29, 2012, is named P4755R1US_ST25.txt and is 5,519 bytes in size.

FIELD OF THE INVENTION

The present invention provides methods of predicting response to a cancer therapy based on gene methylation status.

BACKGROUND OF THE INVENTION

The present invention is directed to methods for diagnosing and treating cancer patients. In particular, the present invention is directed to methods for determining which patients will most benefit from treatment with an epidermal growth factor receptor (EGFR) kinase inhibitor.

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide).

The epidermal growth factor receptor (EGFR) family comprises four closely related receptors (HER1/EGFR, HER2 (ERBB2), HER3 (ERBB23), and HER4 (ERBB4)) involved in cellular responses such as differentiation and proliferation. Over-expression of the EGFR kinase, or its ligand TGF-alpha, is frequently associated with many cancers, including breast, lung, colorectal, ovarian, renal cell, bladder, head and neck cancers, glioblastomas, and astrocytomas, and is believed to contribute to the malignant growth of these tumors. A specific deletion-mutation in the EGFR gene (EGFRvIII) has also been found to increase cellular tumorigenicity. Activation of EGFR stimulated signaling pathways promote multiple processes that are potentially cancer-promoting, e.g. proliferation, angiogenesis, cell motility and invasion, decreased apoptosis and induction of drug resistance. Increased HER1/EGFR expression is frequently linked to advanced disease, metastases and poor prognosis. For example, in NSCLC and gastric cancer, increased HER1/EGFR expression has been shown to correlate with a high metastatic rate, poor tumor differentiation and increased tumor proliferation.

ERBB2 overexpression is commonly regarded as a predictor of a poor prognosis, especially in patients with primary disease that involves axillary lymph nodes ((Slamon et al., Science 235:177-182 (1987); Slamon et al., Science 244:707-712 (1989); Ravdin and Chamness, Gene 159:19-27 (1995); and Hynes and Stern, Biochim Biophys Acta 1198:165-184 (1994), and has been linked to sensitivity and/or resistance to hormone therapy and chemotherapeutic regimens, including CMF (cyclophosphamide, methotrexate, and fluoruracil) and anthracyclines (Baselga et al., Oncology 11(3 Suppl 2):43-48 (1997)). Patients treated with the HER2 antibody trastuzumab are selected for therapy based on HER2 overexpression/amplification. See, for example, WO99/31140, US2003/0170234, WO01/89566.

Mutations which activate the receptor's intrinsic protein tyrosine kinase activity and/or increase downstream signaling have been observed in NSCLC and glioblastoma. However the role of mutations as a principle mechanism in conferring sensitivity to EGF receptor inhibitors, for example erlotinib (TARCEVA®) or gefitinib (IRESSA™), has been controversial. Recently, a mutant form of the full length EGF receptor has been reported to predict responsiveness to the EGF receptor tyrosine kinase inhibitor gefitinib (Paez, J. G. et al. (2004) Science 304:1497-1500; Lynch, T. J. et al. (2004) N. Engl. J. Med. 350:2129-2139). Cell culture studies have shown that cell lines which express the mutant form of the EGF receptor (i.e. H3255) were more sensitive to growth inhibition by the EGF receptor tyrosine kinase inhibitor gefitinib, and that much higher concentrations of gefitinib was required to inhibit the tumor cell lines expressing wild type EGF receptor. These observations suggests that specific mutant forms of the EGF receptor may reflect a greater sensitivity to EGF receptor inhibitors but do not identify a completely non-responsive phenotype.

The development for use as anti-tumor agents of compounds that directly inhibit the kinase activity of the EGFR, as well as antibodies that reduce EGFR kinase activity by blocking EGFR activation, are areas of intense research effort (de Bono J. S. and Rowinsky, E. K. (2002) Trends in Mol. Medicine 8:S19-S26; Dancey, J. and Sausville, E. A. (2003) Nature Rev. Drug Discovery 2:92-313). Several studies have demonstrated, disclosed, or suggested that some EGFR kinase inhibitors might improve tumor cell or neoplasia killing when used in combination with certain other anti-cancer or chemotherapeutic agents or treatments (e.g. Herbst, R. S. et al. (2001) Expert Opin. Biol. Ther. 1:719-732; Solomon, B. et al (2003) Int. J. Radiat. Oncol. Biol. Phys. 55:713-723; Krishnan, S. et al. (2003) Frontiers in Bioscience 8, e1-13; Grunwald, V. and Hidalgo, M. (2003) J. Nat. Cancer Inst. 95:851-867; Seymour L. (2003) Current Opin. Investig. Drugs 4(6):658-666; Khalil, M. Y. et al. (2003) Expert Rev. Anticancer Ther. 3:367-380; Bulgaru, A. M. et al. (2003) Expert Rev. Anticancer Ther. 3:269-279; Dancey, J. and Sausville, E. A. (2003) Nature Rev. Drug Discovery 2:92-313; Ciardiello, F. et al. (2000) Clin. Cancer Res. 6:2053-2063; and Patent Publication No: US 2003/0157104).

Erlotinib (e.g. erlotinib HCl, also known as TARCEVA® or OSI-774) is an orally available inhibitor of EGFR kinase. In vitro, erlotinib has demonstrated substantial inhibitory activity against EGFR kinase in a number of human tumor cell lines, including colorectal and breast cancer (Moyer J. D. et al. (1997) Cancer Res. 57:4838), and preclinical evaluation has demonstrated activity against a number of EGFR-expressing human tumor xenografts (Pollack, V. A. et al (1999) J. Pharmacol. Exp. Ther. 291:739). More recently, erlotinib has demonstrated promising activity in phase I and II trials in a number of indications, including head and neck cancer (Soulieres, D., et al. (2004) J. Clin. Oncol. 22:77), NSCLC (Perez-Soler R, et al. (2001) Proc. Am. Soc. Clin. Oncol. 20:310a, abstract 1235), CRC (Oza, M., et al. (2003) Proc. Am. Soc. Clin. Oncol. 22:196a, abstract 785) and MBC (Winer, E., et al. (2002) Breast Cancer Res. Treat. 76:5115a, abstract 445). In a phase III trial, erlotinib monotherapy significantly prolonged survival, delayed disease progression and delayed worsening of lung cancer-related symptoms in patients with advanced, treatment-refractory NSCLC (Shepherd, F. et al. (2004) J. Clin. Oncology, 22:14S (July 15 Supplement), Abstract 7022). While much of the clinical trial data for erlotinib relate to its use in NSCLC, preliminary results from phase I/II studies have demonstrated promising activity for erlotinib and capecitabine/erlotinib combination therapy in patients with wide range of human solid tumor types, including CRC (Oza, M., et al. (2003) Proc. Am. Soc. Clin. Oncol. 22:196a, abstract 785) and MBC (Jones, R. J., et al. (2003) Proc. Am. Soc. Clin. Oncol. 22:45a, abstract 180). In November 2004 the U.S. Food and Drug Administration (FDA) approved erlotinib for the treatment of patients with locally advanced or metastatic non-small cell lung cancer (NSCLC) after failure of at least one prior chemotherapy regimen. Erlotinib is the only drug in the epidermal growth factor receptor (EGFR) class to demonstrate in a Phase III clinical trial an increase in survival in advanced NSCLC patients.

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well. Additionally, for any given cancer type one frequently cannot predict which patient is likely to respond to a particular treatment, even with newer gene-targeted therapies, such as EGFR kinase inhibitors, thus necessitating considerable trial and error, often at considerable risk and discomfort to the patient, in order to find the most effective therapy.

Thus, there is a need for more efficacious treatment for neoplasia and other proliferative disorders, and for more effective means for determining which tumors will respond to which treatment. Strategies for enhancing the therapeutic efficacy of existing drugs have involved changes in the schedule for their administration, and also their use in combination with other anticancer or biochemical modulating agents. Combination therapy is well known as a method that can result in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone).

Target-specific therapeutic approaches, such as erlotinib, are generally associated with reduced toxicity compared with conventional cytotoxic agents, and therefore lend themselves to use in combination regimens. Promising results have been observed in phase I/II studies of erlotinib in combination with bevacizumab (Mininberg, E. D., et al. (2003) Proc. Am. Soc. Clin. Oncol. 22:627a, abstract 2521) and gemcitabine (Dragovich, T., (2003) Proc. Am. Soc. Clin. Oncol. 22:223a, abstract 895). Recent data in NSCLC phase III trials have shown that first-line erlotinib or gefitinib in combination with standard chemotherapy did not improve survival (Gatzemeier, U., (2004) Proc. Am. Soc. Clin. Oncol. 23:617 (Abstract 7010); Herbst, R. S., (2004) Proc. Am. Soc. Clin. Oncol. 23:617 (Abstract 7011); Giaccone, G., et al. (2004) J. Clin. Oncol. 22:777; Herbst, R., et al. (2004) J. Clin. Oncol. 22:785). However, pancreatic cancer phase III trials have shown that first-line erlotinib in combination with gemcitabine did improve survival.

Several groups have investigated potential biomarkers to predict a patient's response to EGFR inhibitors (see for example, WO 2004/063709, WO 2005/017493, WO 2004/111273, WO 2004/071572; US 2005/0019785, and US 2004/0132097). One such biomarker is epithelial and mesenchymal phenotype. During most cancer metastases, an important change occurs in a tumor cell known as the epithelial-to-mesenchymal transition (EMT) (Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515)). Epithelial cells, which are bound together tightly and exhibit polarity, give rise to mesenchymal cells, which are held together more loosely, exhibit a loss of polarity, and have the ability to travel. These mesenchymal cells can spread into tissues surrounding the original tumor, invade blood and lymph vessels, and travel to new locations where they divide and form additional tumors. EMT does not occur in healthy cells except during embryogenesis. Under normal circumstances TGF-β acts as a growth inhibitor, however, during cancer metastasis, TGF-β begins to promote EMT.

Epithelial and mesenchymal phenotypes have been associated with particular gene expression patterns. For example, epithelial phenotype was shown in WO2006101925 to be associated with high expression levels of E-cadherin, Brk, γ-catenin, α-catenin, keratin 8, keratin 18, connexin 31, plakophilin 3, stratafin 1, laminin alpha-5 and ST14 whereas mesenchymal phenotype was associated with high expression levels of vimentin, fibronectin, fibrillin-1, fibrillin-2, collagen alpha-2(IV), collagen alpha-2(V), LOXL1, nidogen, C11orf9, tenascin, N-cadherin, embryonal EDB+ fibronectin, tubulin alpha-3 and epimorphin.

Epigenetics is the study of heritable changes in gene expression or cellular phenotype caused by mechanisms other than changes in the underlying DNA sequence—hence the name epi-(Greek: over, above, outer)-genetics. Examples of such changes include DNA methylation and histone modifications, both of which serve to modulate gene expression without altering the sequence of the associated genes. These changes can be somatically heritable through cell division for the remainder of the life of the organism and may also be passed on to subsequent generations of the organism. However, there is no change in the underlying DNA sequence of the organism; instead, non-genetic factors cause the organism's genes to behave or express differently.

DNA methylation is a crucial part of normal organismal development and cellular differentiation in higher organisms. DNA methylation stably alters the gene expression pattern in cells such that cells can "remember where they have been"; for example, cells programmed to be pancreatic islets during embryonic development remain pancreatic islets throughout the life of the organism without continuing signals telling them that they need to remain islets. In addition, DNA methylation suppresses the expression of viral genes and other deleterious elements that have been incorporated into the genome of the host over time. DNA methylation also forms the basis of chromatin structure, which enables cells to form the myriad characteristics necessary for multicellular life from a single immutable sequence of DNA. DNA methylation also plays a crucial role in the development of nearly all types of cancer. DNA methylation at the 5 position of cytosine has the specific effect of reducing gene expression and has been found in every vertebrate examined. In adult somatic tissues, DNA methylation typically occurs in a CpG dinucleotide context while non-CpG methylation is prevalent in embryonic stem cells.

"CpG" is shorthand for "—C-phosphate-G-", that is, cytosine and guanine separated by only one phosphate; phosphate links any two nucleosides together in DNA. The "CpG" notation is used to distinguish this linear sequence from the CG base-pairing of cytosine and guanine. Cytosines in CpG dinucleotides can be methylated to form 5-methylcytosine (5-mC). In mammals, methylating the cytosine within a gene can turn the gene off. Enzymes that add a methyl group to DNA are called DNA methyltransferases. In mammals, 70% to 80% of CpG cytosines are methylated. There are regions of the genome that have a higher concentration of CpG sites, known as CpG islands. These "CpG islands" also have a higher than expected GC content (i.e. >50%). Many genes in mammalian genomes have CpG islands associated with the start of the gene. Because of this, the presence of a CpG island is used to help in the prediction and annotation of genes. CpG islands are refractory to methylation, which may help maintain an open chromatin configuration. In addition, this could result in a reduced vulnerability to transition mutations and, as a consequence, a higher equilibrium density of CpGs surviving. Methylation of CpG sites within the promoters of genes can lead to their silencing, a feature found in a number of human cancers (for example the silencing of tumor suppressor genes). In contrast, the hypomethylation of CpG sites has been associated with the over-expression of oncogenes within cancer cells.

SUMMARY OF THE INVENTION

One aspect of the invention provides for a method of determining the sensitivity of tumor cell growth to inhibition by an EGFR kinase inhibitor, comprising detecting the methylation status of the ERBB2 gene in a sample tumor cell, wherein hypomethylation of the ERBB2 gene indicates that the tumor cell growth is sensitive to inhibition with the EGFR inhibitor. Another aspect of the invention provides for a method of identifying a cancer patient who is likely to benefit from treatment with an EFGR inhibitor comprising detecting the methylation status of the ERBB2 gene from a sample from the patient's cancer, wherein the patient is identified as being likely to benefit from treatment with the EGFR inhibitor if the methylation status of the ERBB2 gene is detected to be hypomethylation. In one embodiment, the patient is administered a therapeutically effective amount of an EGFR inhibitor if the patient is identified as one who will likely benefit from treatment with the EGFR inhibitor.

Another aspect of the invention provides for a method of treating a cancer in a patient comprising administering a therapeutically effective amount of an EGFR inhibitor to the patient, wherein the patient, prior to administration of the EGFR inhibitor, was diagnosed with a cancer which exhibits hypomethylation of the ERBB2 gene, wherein the hypomethylation of the ERBB2 gene is indicative of therapeutic responsiveness by the subject to the EGFR inhibitor.

Another aspect of the invention provides for a method of selecting a therapy for a cancer patient, comprising the steps of detecting the methylation status of the ERBB2 gene from a sample from the patient's cancer, and selecting an EGFR inhibitor for the therapy when the ERBB2 gene is detected to be hypomethylated. In one embodiment, the patient is administered a therapeutically effective amount of the EGFR inhibitor, such as, for example, erlotinib, cetuximab, or panitumumab.

Another aspect of the invention provides for a method of determining overexpression of ERBB2 gene in a cell comprising detecting the methylation status of the ERBB2 gene in the cell, wherein ERBB2 gene hypomethylation indicates overexpression of ERBB2 in the cell.

Another aspect of the invention provides for a method of treating a cancer in a patient comprising administering a therapeutically effective amount of a HER2 inhibitor to the patient, wherein the patient, prior to administration of the HER2 inhibitor, was diagnosed with a cancer which exhibits hypomethylation of the ERBB2 gene, wherein the hypomethylation of the ERBB2 gene is indicative of therapeutic responsiveness by the subject to the HER2 inhibitor.

Another aspect of the invention provides for a method of selecting a therapy for a cancer patient, comprising the steps of detecting the methylation status of the ERBB2 gene from a sample from the patient's cancer, and selecting a HER2 inhibitor for the therapy when the ERBB2 gene is detected to be hypomethylated. In one embodiment, the patient is administered a therapeutically effective amount of the HER2 inhibitor, such as trastuzumab or T-DM1.

In certain embodiments of the above methods, the methylation status is detected in a part of the ERBB2 gene. The part of the gene used to detect the methylation status is, for example, an enhancer region, or an enhancer region and a promoter region. In one embodiment, the part of the gene used to detect the methylation status comprises the nucleic acid sequence of SEQ ID NO:1. In one embodiment, the part of the gene used to detect the methylation status consists of the nucleic acid sequence of SEQ ID NO:1. In one embodiment, the part of the gene used to detect the methylation status comprises a 6 CpG repeat region. In one embodiment, the part of the gene used to detect the methylation status comprises the nucleic acid sequence of SEQ ID NO: 2. In one embodiment, the part of the gene used to detect the methylation status consists of the nucleic acid sequence of SEQ ID NO: 2.

In certain embodiments of the methods, the methylation status of the ERBB2 gene is deemed to a hypomethylation status if the ERBB2 gene, or part thereof, is less than about 50% or less than about 20% methylated.

In certain embodiments of the above methods, the methylation status is detected by pyrosequencing. In certain embodiments of the above methods, the ERBB2 gene is from a formalin-fixed paraffin embedded (FFPE) tissue or from fresh frozen tissue. In certain embodiments of the above methods, the ERBB2 gene isolated from the tissue sample is preamplified before pyrosequencing.

In certain embodiments of the above methods, the tumor cell is a NSCLC tumor cell or the cancer is NSCLC.

BRIEF DESCRIPTION OF THE FIGURES

FIG. 1 shows the nucleic acid sequence of the ERBB2 enhancer region (SEQ ID NO: 1) containing 28 CpG methylation sites (SEQ ID NO: 1).

DESCRIPTION OF THE INVENTION

I. Definitions

Figure 2:
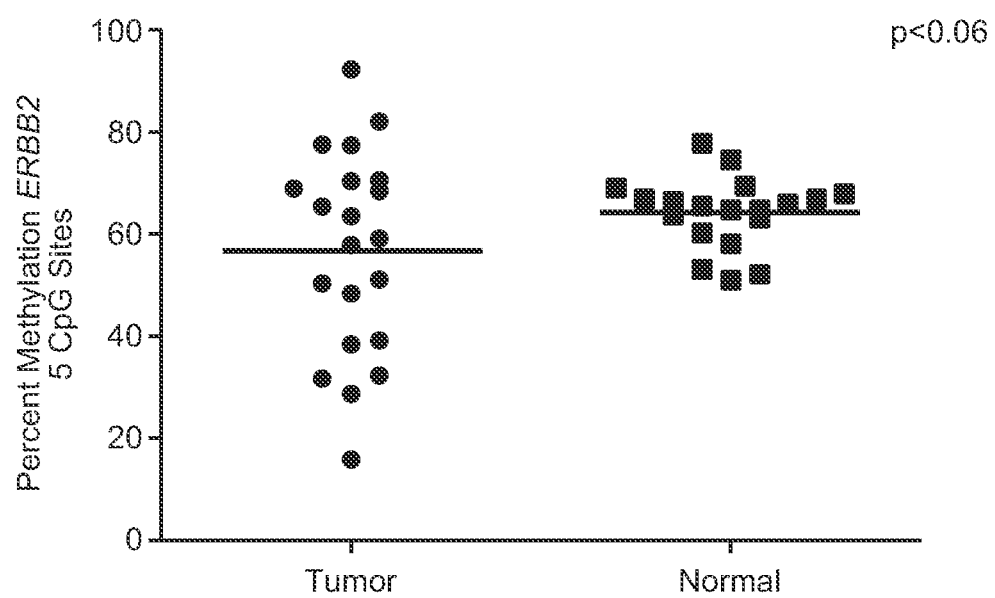
FIG. 2 is a graph depicting the results of a pyrosequencing analysis of ERBB2 methylation status in NSCLC surgically resected primary tumors and matched normal tissue.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Before the present methods, kits and uses therefore are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise.

Throughout this specification and claims, the word "comprise," or variations such as "comprises" or "comprising," will be understood to imply the inclusion of a stated integer or group of integers but not the exclusion of any other integer or group of integers.

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient.

The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer.

"A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The terms "ErbB1", "HER1", "epidermal growth factor receptor" and "EGFR" and "EGFR kinase" are used interchangeably herein and refer to EGFR as disclosed, for example, in Carpenter et al. Ann. Rev. Biochem. 56:881-914 (1987), including naturally occurring mutant forms thereof (e.g. a deletion mutant EGFR as in Humphrey et al. PNAS (USA) 87:4207-4211 (1990)). erbB1 refers to the gene encoding the EGFR protein product.

As used herein, the term "EGFR kinase inhibitor" and "EGFR inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGF receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

Inhibitors of EGF receptor function have shown clinical utility and the definition of key EGF receptor signaling pathways which describe patient subsets most likely to benefit from therapy has become an important area of investigation. Mutations which activate the receptor's intrinsic protein tyrosine kinase activity and/or increase downstream signaling have been observed in NSCLC and glioblastoma. In vitro and clinical studies have shown considerable variability between wt EGF receptor cell lines and tumors in their cellular responses to EGF receptor inhibition, which in part has been shown to derive from EGF receptor independent activation of the phosphatidyl inositol 3-kinase pathway, leading to the continued phosphorylation of the anti-apoptotic serine-threonine kinase Akt. The molecular determinants to alternative routes of PI3-kinase activation and consequent EGF receptor inhibitor insensitivity are an active area of investigation. For example the insulin-like growth factor-1 receptor (IGF-1 receptor), which strongly activates the PI3-kinase pathway, has been implicated in cellular resistance to EGF inhibitors. The roles of cell-cell and cell-adhesion networks, which can also exert survival signals through the PI3-kinase pathway in mediating insensitivity to selective EGF receptor inhibition are less clear and would be postulated to impact cell sensitivity to EGF receptor blockade. The ability of tumor cells to maintain growth and survival signals in the absence of adhesion to extracellular matrix or cell-cell contacts is important not only in the context of cell migration and metastasis but also in maintaining cell proliferation and survival in wound-like tumor environments where extracellular matrix is being remodeled and cell contact inhibition is diminished. We previously defined an EMT gene expression signature that correlates with in vitro sensitivity of NSCLC cell lines to erlotinib (Yauch et al., 2005, Clin Cancer Res 11, 8686-8698).

The expressions "ErbB2" and "HER2" are used interchangeably herein and refer to human HER2 protein described, for example, in Semba et al., PNAS (USA) 82:6497-6501 (1985) and Yamamoto et al. Nature 319:230-234 (1986) (Genebank accession number X03363). The term "erbB2" refers to the gene encoding human ErbB2 and "neu" refers to the gene encoding rat p185neu.

"ErbB3" and "HER3" refer to the receptor polypeptide as disclosed, for example, in U.S. Pat. Nos. 5,183,884 and 5,480,968 as well as Kraus et al. PNAS (USA) 86:9193-9197 (1989).

The terms "ErbB4" and "HER4" herein refer to the receptor polypeptide as disclosed, for example, in EP Pat Appln No 599,274; Plowman et al., Proc. Natl. Acad. Sci. USA, 90:1746-1750 (1993); and Plowman et al., Nature, 366:473-475 (1993), including isoforms thereof, e.g., as disclosed in WO99/19488, published Apr. 22, 1999.

By "hypomethylation" is meant that a majority of the possibly methylated CpG sites are unmethylated. In certain embodiments, hypomethylation means that less than 50%, less than 45%, less than 40%, less than 35%, less than 30%, less than 25%, less than 20%, less than 15%, less than 10%, less than 5%, or less than 1% of the possible methylation sites in a part of the ERBB2 gene is methylated. In one embodiment, the part of the EBB2 gene comprises an enhancer region of ERBB2. In one embodiment, the part of the EBB2 gene comprises the ERBB2 enhancer region of SEQ ID NO: 1, containing 28 CpG methylation sites. In yet another embodiment, hypomethylation means that fewer possible methylation sites are methylated compared to an ERBB2 gene that is expressed at a normal level, for example, in a non-tumor cell. In another embodiment, hypomethylation means that none of the CpG sites in the enhancer region of the ERBB2 gene is methylated.

II. Methods and Compositions

The present invention relates, in part, to the discovery that hypomethylation of the ERBB2 gene correlates with high expression of ERBB2 and sensitivity of cancers to treatment with EGFR kinase inhibitors. Accordingly, the present invention provides a method of determining the sensitivity of a tumor to cell growth inhibition by an EGFR kinase inhibitor in a cancer patient, comprising obtaining a sample of the tumor and analyzing the tumor sample to detect methylation status of ERBB2, wherein detection of a hypomethylation status of ERBB2 indicates that the tumor cell growth is sensitive to inhibition by EGFR inhibitor treatment.

Accordingly, in one embodiment, there is provided a method of determining sensitivity of tumor cell growth to inhibition by an EGFR kinase inhibitor comprising detecting the methylation status of the ERBB2 gene in a sample tumor cell, wherein hypomethylation of the ERBB2 gene indicates that the tumor cell growth is sensitive to inhibition with the EGFR inhibitor.

Another aspect of the the invention provides for a method of identifying a cancer patient who is likely to benefit from treatment with an EFGR inhibitor comprising detecting the methylation status of the ERBB2 gene from a sample from the patient's cancer, such as a sample from a cancerous tumor, wherein the patient is identified as being likely to benefit from treatment with the EGFR inhibitor if the ERBB2 gene is detected to be hypomethylated. In some embodiments, the patient is administered a therapeutically effective amount of the EGFR inhibitor based on the hypomethylation status.

Furthermore, provided herein are methods of identifying an patient who is more likely to exhibit benefit from a therapy with an EGFR inhibitor, the method comprising detecting hypomethylation in a part of the ERBB2 gene, wherein less than about 50%, 45%, 40%, 35%, 30%, 25%, 20%, 15%, 10%, 5%, 2%, or 1% methylation of the analyzed part of the ERBB2 gene sequence indicates that the patient is more likely to benefit from treatment.

Another aspect of the invention provides for a method of selecting a therapy for a cancer patient based on the methylation status of the ERBB2 gene in a sample taken from the patient's cancer, such as a sample of a cancerous tumor. In one embodiment, the method of selecting a therapy comprises the steps of detecting the methylation status of the ERBB2 gene from a sample from the patient's cancer, and selecting an EGFR inhibitor for the therapy when the ERBB2 gene is detected to be hypomethylated (the methylation status is deemed to be a hypomethylated status). The patient is then administered a therapeutically effective amount of the EGFR inhibitor based on this selection method. In some embodiments, the EFGR inhibitor is erlotinib, cetuximab, or panitumumab.

Another aspect of the invention provides for a method of treating a patient with an EGFR inhibitor if the patient is suffering from a cancer characterized by ERBB2 hypomethylation.

Yet another aspect of the invention provides for a method of determining whether the ERBB2 gene is overexpress in a cell, such as a cancer cell, comprising detecting the methylation status of the ERBB2 gene in the cell, wherein a determination that the ERBB2 gene is hypomethylated indicates overexpression of ERBB2 in the cell.

Overexpression of the ERBB2 gene has been previously correlated to response to HER2 inhibitors, such as trastuzumab (HERCEPTIN®, Genentech, Inc.) and T-DM1. See, for example, WO99/31140, US2003/0170234, WO01/89566. As such, another aspect of the invention provides for a method of treating a patient with an HER2 inhibitor if the patient is suffering from a cancer characterized by ERBB2 hypomethylation. Accordingly, provided herein are methods of identifying an individual who is more likely to exhibit benefit from a therapy comprising an HER2 inhibitor, the method comprising detecting hypomethylation in a part of the ERBB2 gene, wherein less than about 50%, 45%, 40%, 35%, 30%, 25%, 20%, 15%, 10%, 5%, 2%, or 1% methylation of the ERBB2 sequence indicates that the individual is more likely to benefit from treatment.

In one embodiment, the invention provides a method of treating cancer in a patient comprising administering a therapeutically effective amount of a HER2 inhibitor to the patient, wherein the patient, prior to administration of the HER2 inhibitor, was diagnosed with a cancer characterized by ERBB2 hypomethylation, wherein the ERBB2 hypomethylation is indicative of therapeutic responsiveness by the subject to the HER2 inhibitor. In one embodiment, the HER2 inhibitor is a small molecule or an antibody. In one embodiment, the HER2 inhibitor is an antibody such as trastuzumab or T-DM1.

Another aspect of the invention provides for a method of selecting a therapy for a cancer patient, comprising the steps of detecting the methylation status of the ERBB2 gene from a sample from the patient's cancer and selecting a HER2 inhibitor for the therapy when the ERBB2 gene is detected to be hypomethylated.

In some embodiments of the above methods of detecting methylation status of the ERBB2 gene, the part of the ERBB2 gene analyzed for methylation status comprises an enhancer region. In some embodiments, the part of the ERBB2 gene comprises an enhancer region and a promoter region. In some embodiments, the part of the ERBB2 gene is part of the gene at or comprising the chromosomal location of chr17:37,861,100-37,863,650 (NCBI build 37/hg19). In some embodiments, the part of the ERBB2 gene is the sequence represented by SEQ ID NO:1. In some embodiments, the part of the ERBB2 gene comprises a 6 CpG repeat region of SEQ ID NO:1. In one embodiment, the part of the ERBB2 gene comprises the 6 CpG repeat region of SEQ ID NO: 2.

In some embodiments, the part of the ERBB2 gene is pre-amplified prior to quantitative methylation specific PCR.

In certain embodiments of the above methods, the methylation status of the ERBB2 gene or a specific part of the gene is deemed to be hypomethylated when less than about 50%, 45%, 40%, 35%, 30%, 25%, 20%, 15%, 10%, 5%, 2%, or 1% methylation of the analyzed part of the ERBB2 gene sequence is detected.

Presence and/or level/amount of various biomarkers in a sample can be analyzed by a number of methodologies, many of which are known in the art and understood by the skilled artisan, including, but not limited to, immunohistochemical ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

Methods for evaluation of DNA methylation are well known. For example, Laird (2010) Nature Reviews Genetics 11:191-203 provides a review of DNA methylation analysis. In some embodiments, methods for evaluating methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. In some embodiments, the method can encompass amplifying intact DNA after restriction enzyme digestion, thereby only amplifying DNA that was not cleaved by the restriction enzyme in the area amplified. See, e.g., U.S. patent application Ser. Nos. 10/971,986; 11/071,013; and 10/971,339. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In some embodiments, a second step can be performed to determine the presence, absence or quantity of a particular gene in an amplified pool of DNA. In some embodiments, the DNA is amplified using real-time, quantitative PCR.

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. patent application Ser. No. 10/971,986.

In some embodiments, quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., Gibson et al., Genome Research 6:995-1001 (1996); DeGraves et al., Biotechniques 34(1):106-10, 112-5 (2003); Deiman B et al., Mol Biotechnol. 20(2):163-79 (2002).

Additional methods for detecting DNA methylation can involve genomic sequencing before and after treatment of the DNA with bisulfate. See, e.g., Frommer et al., Proc. Natl. Acad. Sci. USA 89:1827-1831 (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby, Nucl. Acids Res. 24:5058-5059 (1996); Xiong & Laird, Nucleic Acids Res. 25:2532-2534 (1997).

In some embodiments, a MethyLight assay is used alone or in combination with other methods to detect DNA methylation (see, Eads et al., Cancer Res. 59:2302-2306 (1999)). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of an unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, a Ms-SNuPE (Methylation-sensitive Single Nucleotide Primer Extension) reaction is used alone or in combination with other methods to detect DNA methylation (see Gonzalgo & Jones Nucleic Acids Res. 25:2529-2531 (1997)). The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated versus unmethylated DNA. See, Herman et al., Proc. Natl. Acad. Sci. USA 93:9821-9826, (1996); U.S. Pat. No. 5,786,146. In some embodiments, DNA methylation is detected by a QIAGEN PyroMark CpG Assay predesigned Pyrosequencing DNA Methylation assays.

In some embodiments, cell methylation status is determined using high-throughput DNA methylation analysis to determine sensitivity to EGFR inhibitors. Briefly, genomic DNA is isolated from a cell or tissue sample (e.g. a tumor sample or a blood sample) and is converted in a sodium bisulfite reaction (the bisulfite process converts unmethylated cytosine residues to uracil) using standard assays in the art. The bisulfite converted DNA product is amplified, fragmented and hybridized to an array containing CpG sites from across a genome using standard assays in the art. Following hybridization, the array is imaged and processed for analysis of the DNA methylation status using standard assays in the art. In some embodiments, the tissue sample is formalin-fixed paraffin embedded (FFPE) tissue. In some embodiments, the tissue sample is fresh frozen tissue. In some embodiments, the DNA isolated from the tissue sample is preamplified before bisulfite conversion. In some embodiments, the DNA isolated from the tissue sample is preamplified before bisulfite conversion by using the Invitrogen Superscript III One-Step RT-PCR System with Platinum Taq. In some embodiments, the DNA isolated from the tissue sample is preamplified before bisulfite conversion using a Taqman based assay. In some embodiments, the sodium bisulfite reaction is conducted using the Zymo EZ DNA Methylation Kit. In some embodiments, the bisulfite converted DNA is amplified and hybridized to an array using the Illumina Infinium HumanMethylation450 Beadchip Kit. In some embodiments, the array is imaged on an Illumina iScan Reader. In some embodiments, the images are processed with the Genome Studio software methylation module. In some embodiments, the methylation data is analyzed using the Bioconductor lumi software package. See Du et al., Bioinformatics, 24(13):1547-1548 (2008).

In some embodiments, ERBB2 DNA methylation sites are identified using bisulfite sequencing PCR (BSP) to determine sensitivity to EGFR inhibitors. Briefly, genomic DNA is isolated from a cell or tissue sample (e.g., a tumor sample or a blood sample) and is converted in a sodium bisulfite reaction (the bisulfite process converts unmethylated cytosine residues to uracil) using standard assays in the art. The bisulfite converted DNA product is amplified using primers designed to be specific to the bisulfite converted DNA (e.g., bisulfite-specific primers) and ligated into vectors for transformation into a host cell using standard assays in the art. After selection of the host cells containing the PCR amplified bisulfite converted DNA product of interest, the DNA product is isolated and sequenced to determine the sites of methylation using standard assays in the art. In some embodiments, the tissue sample is formalin-fixed paraffin embedded (FFPE) tissue. In some embodiments, the tissue sample is an FFPE tissue that has been processed for IHC analysis; for example, for ERBB2 expression. In some embodiments, the tissue sample is an FFPE tissue that showed little or no ERBB2 expression by IHC. In some embodiments, the tissue sample is fresh frozen tissue. In some embodiments, the DNA isolated from the tissue sample is preamplified before bisulfite conversion. In some embodiments, the DNA isolated from the tissue sample is preamplified before bisulfite conversion using the Invitrogen Superscript III One-Step RT-PCR System with Platinum Taq. In some embodiments, the DNA isolated from the tissue sample is preamplified before bisulfite conversion using a Taqman based assay. In some embodiments, the sodium bisulfite reaction is conducted using the Zymo EZ DNA Methylation-Gold Kit. In some embodiments, the primers designed to be specific to the bisulfite converted DNA are designed using Applied Biosystems Methyl Primer Express software. In some embodiments, the bisulfite converted DNA product is PCR amplified using the Invitrogen Superscript III One-Step RT-PCR System with Platinum Taq. In further embodiments, the PCR amplified bisulfite converted DNA product is ligated into a vector using the Invitrogen TOPO TA Cloning kit. In some embodiments, the host cell is bacteria. In some embodiments, the isolated PCR amplified bisulfite converted DNA product of interest is sequenced using Applied Biosystems 3730x1 DNA Analyzer. In some embodiments, the primers designed to be specific to the bisulfite converted DNA are designed using Qiagen PyroMark Assay Design software. In some embodiments, the bisulfite converted DNA product is PCR amplified using the Invitrogen Superscript III One-Step RT-PCR System with Platinum Taq. In further embodiments, the PCR amplified bisulfite converted DNA product is sequenced using Qiagen Pyromark Q24 and analyzed Qiagen with PyroMark software.

In some embodiments, ERBB2 DNA methylation sites are identified using quantitative methylation specific PCR (QMSP) to determine sensitivity to EGFR or HER2 inhibitors. Briefly, genomic DNA is isolated from a cell or tissue sample and is converted in a sodium bisulfite reaction (the bisulfite process converts unmethylated cytosine residues to uracil) using standard assays in the art. In some embodiments, the tissue sample is formalin-fixed paraffin embedded (FFPE) tissue. In some embodiments, the tissue sample is an FFPE tissue that has been processed for IHC analysis; for example, for ERBB2 expression. In some embodiments, the tissue sample is an FFPE tissue that showed little or no ERBB2 expression by IHC. In some embodiments, the tissue sample is fresh frozen tissue. The bisulfite converted DNA product is amplified using primers designed to be specific to the bisulfite converted DNA (e.g., quantitative methylation specific PCR primers). The bisulfite converted DNA product is amplified with quantitative methylation specific PCR primers and analyzed for methylation using standard assays in the art. In some embodiments, the tissue sample is formalin-fixed paraffin embedded (FFPE) tissue. In some embodiments, the tissue sample is fresh frozen tissue. In some embodiments, the DNA isolated from the tissue sample is preamplified before bisulfite conversion using the Invitrogen Superscript III One-Step RT-PCR System with Platinum Taq. In some embodiments, the DNA isolated from the tissue sample is preamplified before bisulfite conversion. In some embodiments, the DNA isolated from the tissue sample is preamplified before bisulfite conversion using a Taqman based assay. In some embodiments, the sodium bisulfite reaction is conducted using a commercially available kit. In some embodiments, the sodium bisulfite reaction is conducted using the Zymo EZ DNA Methylation-Gold Kit. In some embodiments, the primers designed to be specific to the bisulfite converted DNA are designed using Applied Biosystems Methyl Primer Express software. In some embodiments, the bisulfite converted DNA is amplified using a Taqman based assay. In some embodiments, the bisulfite converted DNA is amplified on an Applied Biosystems 7900HT and analyzed using Applied Biosystems SDS software.

In some embodiments, the invention provides methods to determine ERBB2 methylation by 1) IHC analysis of tumor samples, followed by 2) quantitative methylation specific PCR of DNA extracted from the tumor tissue used in the IHC analysis of step 1. Briefly, coverslips from IHC slides are removed by one of two methods: the slide are placed in a freezer for at least 15 minutes, then the coverslip is pried off of the microscope slide using a razor blade. Slides are then incubated in xylene at room temp to dissolve the mounting media. Alternatively, slides are soaked in xylene until the coverslip falls off. This can take up to several days. All slides are taken through a deparaffinization procedure of 5 min xylene (×3), and 5 min 100% ethanol (×2). Tissues are scraped off slides with razor blades and placed in a tissue lysis buffer containing proteinase K and incubated overnight at 56° C. In cases where tissue is still present after incubation, an extra 10 µl Proteinase K may be added and the tissue is incubated for another 30 min. DNA extraction was continued; for example, by using a QIAamp DNA FFPE Tissue kit. DNA extracted directly from IHC slides was subject to QMSP analysis using the QMSP3 primers and probes as described above.

In some embodiments, the bisulfite-converted DNA is sequenced by a deep sequencing. Deep sequencing is a process, such as direct pyrosequencing, where a sequence is read multiple times. Deep sequencing can be used to detect rare events such as rare mutations. Ultra-deep sequencing of a limited number of loci may been achieved by direct pyrosequencing of PCR products and by sequencing of more than 100 PCR products in a single run. A challenge in sequencing bisulphite-converted DNA arises from its low sequence complexity following bisulfite conversion of cytosine residues to thymine (uracil) residues. Reduced representation bisulphite sequencing (RRBS) may be introduced to reduce sequence redundancy by selecting only some regions of the genome for sequencing by size-fractionation of DNA fragments (Laird, P W Nature Reviews 11:195-203 (2010)). Targeting may be accomplished by array capture or padlock capture before sequencing. For example, targeted capture on fixed arrays or by solution hybrid selection can enrich for sequences targeted by a library of DNA or RNA oligonucleotides and can be performed before or after bisulphite conversion. Alternatively, padlock capture provides improved enrichment efficiency by combining the increased annealing specificity of two tethered probes, and subsequent amplification with universal primers allows for a more uniform representation than amplification with locus-specific primers.

Additional methylation detection methods include, but are not limited to, methylated CpG island amplification (see Toyota et al., Cancer Res. 59:2307-12 (1999)) and those described in, e.g., U.S. Patent Publication 2005/0069879; Rein et al., Nucleic Acids Res. 26 (10): 2255-64 (1998); Olek et al., Nat Genet. 17(3): 275-6 (1997); Laird, P W Nature Reviews 11:195-203 (2010); and PCT Publication No. WO 00/70090).

In some embodiments, the expression of ERBB2 in a cell is determined by evaluating ERBB2 mRNA in a cell. Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like). In some embodiments, the expression of ERBB2 in a test sample is compared to a reference sample. For example, the test sample may be a tumor tissue sample and the reference sample may be from normal tissue or cells such as PBMCs.

Samples from mammals can be conveniently assayed for mRNAs using Northern, dot blot or PCR analysis. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods of the invention include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of anti-angiogenic therapy may be arrayed on a solid support. Hybridization of a labeled probe with a particular array member indicates that the sample from which the probe was derived expresses that gene.

According to some embodiments, presence and/or level/amount is measured by observing protein expression levels of an aforementioned gene. In certain embodiments, the method comprises contacting the biological sample with antibodies to a biomarker described herein under conditions permissive for binding of the biomarker, and detecting whether a complex is formed between the antibodies and biomarker. Such method may be an in vitro or in vivo method.

In certain embodiments, the presence and/or level/amount of biomarker proteins in a sample are examined using IHC and staining protocols. IHC staining of tissue sections has been shown to be a reliable method of determining or detecting presence of proteins in a sample. In one aspect, level of biomarker is determined using a method comprising: (a) performing IHC analysis of a sample (such as a subject cancer sample) with an antibody; and b) determining level of a biomarker in the sample. In some embodiments, IHC staining intensity is determined relative to a reference value.

IHC may be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) Radioisotopes, such as $^{35}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see U.S. Pat. Nos. 4,275,149 and 4,318,980.

Specimens thus prepared may be mounted and coverslipped. Slide evaluation is then determined, e.g., using a microscope, and staining intensity criteria, routinely used in the art, may be employed. In some embodiments, a staining pattern score of about 1+ or higher is diagnostic and/or prognostic. In certain embodiments, a staining pattern score of about 2+ or higher in an IHC assay is diagnostic and/or prognostic. In other embodiments, a staining pattern score of about 3 or higher is diagnostic and/or prognostic. In one embodiment, it is understood that when cells and/or tissue from a tumor or colon adenoma are examined using IHC, staining is generally determined or assessed in tumor cell and/or tissue (as opposed to stromal or surrounding tissue that may be present in the sample).

In alternative methods, the sample may be contacted with an antibody specific for the biomarker under conditions sufficient for an antibody-biomarker complex to form, and then detecting the complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Presence and/or level/amount of a selected biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

In certain embodiments, the samples are normalized for both differences in the amount of the biomarker assayed and variability in the quality of the samples used, and variability between assay runs. Such normalization may be accomplished by detecting and incorporating the level of certain normalizing biomarkers, including well known housekeeping genes, such as ACTB. Alternatively, normalization can be based on the mean or median signal of all of the assayed genes or a large subset thereof (global normalization approach). On a gene-by-gene basis, measured normalized amount of a subject tumor mRNA or protein is compared to the amount found in a reference set. Normalized expression levels for each mRNA or protein per tested tumor per subject can be expressed as a percentage of the expression level measured in the reference set. The presence and/or expression level/amount measured in a particular subject sample to be analyzed will fall at some percentile within this range, which can be determined by methods well known in the art.

In certain embodiments, relative expression level of a gene is determined as follows:

Relative expression gene1 sample1=2 exp (Ct housekeeping gene−Ct gene1) with Ct determined in a sample.

Relative expression gene1 reference RNA=2 exp (Ct housekeeping gene−Ct gene1) with Ct determined in the reference sample.

Normalized relative expression gene1 sample1=(relative expression gene1 sample1/relative expression gene1 reference RNA)×100

Ct is the threshold cycle. The Ct is the cycle number at which the fluorescence generated within a reaction crosses the threshold line.

All experiments are normalized to a reference RNA, which is a comprehensive mix of RNA from various tissue sources (e.g., reference RNA #636538 from Clontech, Mountain View, Calif.). Identical reference RNA is included in each qRT-PCR run, allowing comparison of results between different experimental runs.

In one embodiment, the sample is a clinical sample. In another embodiment, the sample is used in a diagnostic assay. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood. In some embodiments, the sample includes circulating tumor cells; for example, circulating cancer cells in blood, urine or sputum. Genes or gene products can be detected from cancer or tumor tissue or from other body samples such as urine, sputum, serum or plasma. The same techniques discussed above for detection of target genes or gene products in cancerous samples can be applied to other body samples. Cancer cells may be sloughed off from cancer lesions and appear in such body samples. By screening such body samples, a simple early diagnosis can be achieved for these cancers. In addition, the progress of therapy can be monitored more easily by testing such body samples for target genes or gene products.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the subject or individual. In certain embodiments, a reference sample, reference cell, reference tissue, control sample, control cell, or control tissue is a combined multiple samples from one or more individuals with a disease or disorder (e.g., cancer) who are not the subject or individual. In certain embodiments, a reference sample, reference cell, reference tissue, control sample, control cell, or control tissue is pooled RNA samples from normal tissues or pooled plasma or serum samples from one or more individuals who are not the subject or individual. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the subject or individual.

In the methods of this invention, the tissue samples may be bodily fluids or excretions such as blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor epithelial or mesenchymal biomarkers in such bodily fluids or excretions can sometimes be preferred in circumstances where an invasive sampling method is inappropriate or inconvenient.

In the methods of this invention, the tumor cell can be a lung cancer tumor cell (e.g. non-small cell lung cancer (NSCLC)), a pancreatic cancer tumor cell, a breast cancer tumor cell, a head and neck cancer tumor cell, a gastric cancer tumor cell, a colon cancer tumor cell, an ovarian cancer tumor cell, or a tumor cell from any of a variety of other cancers as described herein below. The tumor cell is preferably of a type known to or expected to express EGFR, as do all tumor cells from solid tumors. The EGFR kinase can be wild type or a mutant form.

In the methods of this invention, the tumor can be a lung cancer tumor (e.g. non-small cell lung cancer (NSCLC)), a pancreatic cancer tumor, a breast cancer tumor, a head and neck cancer tumor, a gastric cancer tumor, a colon cancer tumor, an ovarian cancer tumor, or a tumor from any of a variety of other cancers as described herein below. The tumor is preferably of a type whose cells are known to or expected to express EGFR, as do all solid tumors. The EGFR can be wild type or a mutant form.

Inhibitors and Pharmaceutical Compositions

Exemplary EGFR kinase inhibitors suitable for use in the invention include, for example quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of the EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl) amine (also known as OSI-774, erlotinib, or TARCEVA™ (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or IRESSA™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl) amine (i.e. erlotinib), its hydrochloride salt (i.e. erlotinib HCl, TARCEVA™), or other salt forms (e.g. erlotinib mesylate).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

A variety of HER2 inhibitors are known in the art. These inhibitors include anti-HER2 antibodies. Such antibodies are preferably monoclonal antibodies. They may either be so-called chimaeric antibodies, humanized antibodies or fully human antibodies. Examples of humanized anti-HER2 antibodies are known under the INN names Trastuzumab and Pertuzumab. Trastuzumab is sold by Genentech Inc. and F. Hoffmann-La Roche Ltd under the trade name HERCEPTIN®. Trastuzumab is an antibody that has antigen binding residues of, or derived from, the murine 4D5 antibody (ATCC CRL 10463, deposited with American Type Culture Collection, 12301 Parklawn Drive, Rockville, Md. 20852 under the Budapest Treaty on May 24, 1990). Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337.

Another suitable anti-HER2 antibody is trastuzumab-MCC-DM1 (T-DM1), an antibody-drug conjugate (CAS Reg. No. 139504-50-0), which has the structure:

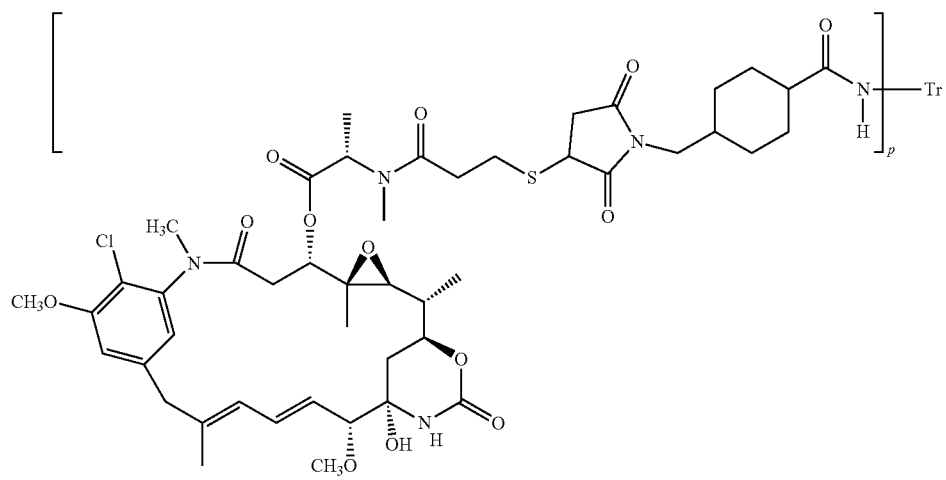

where Tr is trastuzumab, linked through linker moiety MCC, to the maytansinoid drug moiety, DM1 (U.S. Pat. Nos. 5,208,020; 6,441,163). The drug to antibody ratio or drug loading is represented by p in the above structure of trastuzumab-MCC-DM1, and ranges in integer values from 1 to about 8. The drug loading value p is 1 to 8. Trastuzumab-MCC-DM1 includes all mixtures of variously loaded and attached antibody-drug conjugates where 1, 2, 3, 4, 5, 6, 7, and 8 drug moieties are covalently attached to the antibody trastuzumab (U.S. Pat. No. 7,097,840; US 2005/0276812; US 2005/0166993).

Other HER2 antibodies with various properties have been described in Tagliabue et al., Int. J. Cancer, 47:933-937 (1991); McKenzie et al., Oncogene, 4:543-548 (1989); Cancer Res., 51:5361-5369 (1991); Bacus et al., Molecular Carcinogenesis, 3:350-362 (1990); Stancovski et al., PNAS (USA), 88:8691-8695 (1991); Bacus et al, Cancer Research, 52:2580-2589 (1992); Xu et al., Int. J. Cancer, 53:401-408 (1993); WO94/00136; Kasprzyk et al., Cancer Research, 52:2771-2776 (1992); Hancock et al., Cancer Res., 51:4575-4580 (1991); Shawver et al., Cancer Res., 54:1367-1373 (1994); Arteaga et al., Cancer Res., 54:3758-3765 (1994); Harwerth et al., J. Biol. Chem., 267:15160-15167 (1992); U.S. Pat. No. 5,783,186; and Klapper et al., Oncogene, 14:2099-2109 (1997). Further details on the HER2 antigen and antibodies directed thereto are described in many patent and non-patent publications (for a suitable overview see U.S. Pat. No. 5,821,337 and WO 2006/044908).

The methods of this invention can be extended to those compounds which inhibit EGFR and an additional target. These compounds are referred to herein as "bispecific inhibitors". In one embodiment, the bispecific inhibitor is a bispecific HER3/EGFR, EGFR/HER2, EGFR/HER4 or EGFR c-Met, inhibitor. In one embodiment, the bispecific inhibitor is a bispecific antibody. In one embodiment, the bispecific inhibitor is a bispecific antibody which comprises an antigen binding domain that specifically binds to EGFR and a second target. In one embodiment, the bispecific inhibitor is a bispecific antibody which comprises an antigen binding domain that specifically binds to HER3 and EGFR. In one embodiment, the bispecific HER3/EGFR inhibitor is a bispecific antibody which comprises two identical antigen binding domains. Such antibodies are described in U.S. Pat. No. 8,193,321, 20080069820, WO2010108127, US20100255010 and Schaefer et al, Cancer Cell, 20: 472-486 (2011). In one embodiment, the bispecific HER2/EGFR is lapatinib/GW572016.

Additional antibody-based inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce single chain antibodies with desired specificity. Antibody-based inhibitors useful in practicing the present invention also include antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-EGFR antibodies and antibody fragments can also be prepared according to known techniques such as those described in Vaughn, T. J. et al., 1998, Nature Biotech.

16:535-539 and references cited therein, and such antibodies or fragments thereof are also useful in practicing the present invention.

Inhibitors for use in the present invention can alternatively be based on antisense oligonucleotide constructs. Anti-sense oligonucleotides, including anti-sense RNA molecules and anti-sense DNA molecules, would act to directly block the translation of target mRNA by binding thereto and thus preventing protein translation or increasing mRNA degradation, thus decreasing the level of the target protein, and thus activity, in a cell. For example, antisense oligonucleotides of at least about 15 bases and complementary to unique regions of the mRNA transcript sequence encoding EGFR or HER2 can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors for use in the present invention. Target gene expression can be reduced by contacting the tumor, subject or cell with a small double stranded RNA (dsRNA), or a vector or construct causing the production of a small double stranded RNA, such that expression of the target gene is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24):3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

In the context of the methods of treatment of this invention, inhibitors (such as an EGFR inhibitor or a HER2 inhibitor) are used as a composition comprised of a pharmaceutically acceptable carrier and a non-toxic therapeutically effective amount of an EGFR kinase inhibitor compound (including pharmaceutically acceptable salts thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound used in the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Pharmaceutical compositions used in the present invention comprising an inhibitor compound (including pharmaceutically acceptable salts thereof) as active ingredient, can include a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy In practice, the inhibitor compounds (including pharmaceutically acceptable salts thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an inhibitor compound (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

An inhibitor compound (including pharmaceutically acceptable salts thereof) used in this invention, can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, the pharmaceutical composition can comprise an inhibitor compound in combination with an anticancer agent, wherein the anticancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition used for this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions used in the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions used in the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions for the present invention can be in a form suitable for topical sue such as, for example, an aerosol, cream, ointment, lotion, dusting powder, or the like. Further, the compositions can be in a form suitable for use in transdermal devices. These formulations may be prepared, utilizing an inhibitor compound (including pharmaceutically acceptable salts thereof), via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions for this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an inhibitor compound (including pharmaceutically acceptable salts thereof) may also be prepared in powder or liquid concentrate form.

Dosage levels for the compounds used for practicing this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Many alternative experimental methods known in the art may be successfully substituted for those specifically described herein in the practice of this invention, as for example described in many of the excellent manuals and textbooks available in the areas of technology relevant to this invention (e.g. Using Antibodies, A Laboratory Manual, edited by Harlow, E. and Lane, D., 1999, Cold Spring Harbor Laboratory Press, (e.g. ISBN 0-87969-544-7); Roe B. A. et. al. 1996, DNA Isolation and Sequencing (Essential Techniques Series), John Wiley & Sons. (e.g. ISBN 0-471-97324-0); Methods in Enzymology: Chimeric Genes and Proteins", 2000, ed. J. Abelson, M. Simon, S. Emr, J. Thorner. Academic Press; Molecular Cloning: a Laboratory Manual, 2001, 3rd Edition, by Joseph Sambrook and Peter MacCallum, (the former Maniatis Cloning manual) (e.g. ISBN 0-87969-577-3); Current Protocols in Molecular Biology, Ed. Fred M. Ausubel, et. al. John Wiley & Sons (e.g. ISBN 0-471-50338-X); Current Protocols in Protein Science, Ed. John E. Coligan, John Wiley & Sons (e.g. ISBN 0-471-11184-8); and Methods in Enzymology: Guide to protein Purification, 1990, Vol. 182, Ed. Deutscher, M. P., Acedemic Press, Inc. (e.g. ISBN 0-12-213585-7)), or as described in the many university and commercial websites devoted to describing experimental methods in molecular biology.

It will be appreciated by one of skill in the medical arts that the exact manner of administering to the patient of a therapeutically effective amount of an inhibitor as described herein (for example an EGFR kinase inhibitor, bispecific EGFR kinase inhibitor, or HER2 inhibitor) following a diagnosis of a patient's likely responsiveness to the inhibitor will be at the discretion of the attending physician. The mode of administration, including dosage, combination with other anti-cancer agents, timing and frequency of administration, and the like, may be affected by the diagnosis of a patient's likely responsiveness to the inhibitor, as well as the patient's condition and history. Thus, even patients diagnosed with tumors predicted to be relatively insensitive to the type of inhibitor may still benefit from treatment with such inhibitor, particularly in combination with other anti-cancer agents, or agents that may alter a tumor's sensitivity to the inhibitor.

For purposes of the present invention, "co-administration of" and "co-administering" an inhibitor with an additional anti-cancer agent (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The additional agent can be administered prior to, at the same time as, or subsequent to administration of the inhibitor, or in some combination thereof. Where the inhibitor is administered to the patient at repeated intervals, e.g., during a standard course of treatment, the additional agent can be administered prior to, at the same time as, or subsequent to, each administration of the inhibitor, or some combination thereof, or at different intervals in relation to the inhibitor treatment, or in a single dose prior to, at any time during, or subsequent to the course of treatment with the inhibitor.

The inhibitor will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the inhibitor can be administered in any effective manner known in the art, such as by oral, topical, intravenous, intra-peritoneal, intramuscular, intra-articular, subcutaneous, intranasal, intraocular, vaginal, rectal, or intradermal routes, depending upon the type of cancer being treated, the type of inhibitor being used (for example, small molecule, antibody, RNAi, ribozyme or antisense construct), and the medical judgement of the prescribing physician as based, e.g., on the results of published clinical studies.

The amount of inhibitor administered and the timing of inhibitor administration will depend on the type (species, gender, age, weight, etc.) and condition of the patient being treated, the severity of the disease or condition being treated, and on the route of administration. For example, small molecule inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforethe range may be more than adequate, while in other cases still larger doses may be employed without causing any harmful side effect, provided that such larger doses are first divided into several small doses for administration throughout the day.

The inhibitors and other additional agents can be administered either separately or together by the same or different routes, and in a wide variety of different dosage forms. For example, the inhibitor is preferably administered orally or parenterally. Where the inhibitor is erlotinib HCl (TARCEVA™), oral administration is preferable. Both the inhibitor and other additional agents can be administered in single or multiple doses.

The inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The inhibitor can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous inhibitors should be selected so as to avoid denaturation and/or degradation and loss of biological activity of the inhibitor.

Methods of preparing pharmaceutical compositions comprising an inhibitor are known in the art, and are described, e.g. in International Patent Publication No. WO 01/34574. In view of the teaching of the present invention, methods of preparing pharmaceutical compositions comprising an inhibitor will be apparent from the above-cited publications and from other known references, such as Remington's Pharmaceutical Sciences, Mack Publishing Company, Easton, Pa., $18^{th}$ edition (1990).

For oral administration of inhibitors, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising an inhibitor in about 0.1% (w/v) to about 5% (w/v) concentration can be prepared.

For veterinary purposes, the active agents can be administered separately or together to animals using any of the forms and by any of the routes described above. In a preferred embodiment, the inhibitor is administered in the form of a capsule, bolus, tablet, liquid drench, by injection or as an implant. As an alternative, the inhibitor can be administered with the animal feedstuff, and for this purpose a concentrated feed additive or premix may be prepared for a normal animal feed. Such formulations are prepared in a conventional manner in accordance with standard veterinary practice.

One of skill in the medical arts, particularly pertaining to the application of diagnostic tests and treatment with therapeutics, will recognize that biological systems may exhibit variability and may not always be entirely predictable, and thus many good diagnostic tests or therapeutics are occasionally ineffective. Thus, it is ultimately up to the judgement of the attending physician to determine the most appropriate course of treatment for an individual patient, based upon test results, patient condition and history, and his own experience. There may even be occasions, for example, when a physician will choose to treat a patient with an EGFR inhibitor even when a tumor is not predicted to be particularly sensitive to EGFR kinase inhibitors, based on data from diagnostic tests or from other criteria, particularly if all or most of the other obvious treatment options have failed, or if some synergy is anticipated when given with another treatment. The fact that the EGFR inhibitors as a class of drugs are relatively well tolerated compared to many other anti-cancer drugs, such as more traditional chemotherapy or cytotoxic agents used in the treatment of cancer, makes this a more viable option.

Methods of Advertising

The invention herein also encompasses a method for advertising an EGFR or HER2 inhibitor, or a pharmaceutically acceptable composition thereof comprising promoting, to a target audience, the use of the inhibitor or pharmaceutical composition thereof for treating a patient population with a type of cancer which is characterized by ERBB2 hypomethylation.

Advertising is generally paid communication through a non-personal medium in which the sponsor is identified and the message is controlled. Advertising for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The advertising and promotion of the diagnostic method herein may be accomplished by any means. Examples of advertising media used to deliver these messages include television, radio, movies, magazines, newspapers, the internet, and billboards, including commercials, which are messages appearing in the broadcast media. Advertisements also include those on the seats of grocery carts, on the walls of an airport walkway, and on the sides of buses, or heard in telephone hold messages or in-store PA systems, or anywhere a visual or audible communication can be placed.

More specific examples of promotion or advertising means include television, radio, movies, the internet such as webcasts and webinars, interactive computer networks intended to reach simultaneous users, fixed or electronic billboards and other public signs, posters, traditional or electronic literature such as magazines and newspapers, other media outlets, presentations or individual contacts by, e.g., e-mail, phone, instant message, postal, courier, mass, or carrier mail, in-person visits, etc.

The type of advertising used will depend on many factors, for example, on the nature of the target audience to be reached, e.g., hospitals, insurance companies, clinics, doctors, nurses, and patients, as well as cost considerations and the relevant jurisdictional laws and regulations governing advertising of medicaments and diagnostics. The advertising may be individualized or customized based on user characterizations defined by service interaction and/or other data such as user demographics and geographical location.

This invention will be better understood from the Examples that follow. However, one skilled in the art will readily appreciate that the specific methods and results discussed are merely illustrative of the invention as described more fully in the claims which follow thereafter, and are not to be considered in any way limited thereto.

All patents, published patent applications and other references disclosed herein are hereby expressly incorporated by reference in their entirety.

III. Examples

Example 1—Materials and Methods

Cell Lines:

All of the NSCLC cell lines were purchased from the American Type Cell Culture Collection (ATCC) or were provided by Adi Gazdar and John Minna at UT Southwestern. The immortalized bronchial epithelial (gBECs) and small airway (gSACs) cell lines were created at Genentech using a tricistronic vector containing cdk4, hTERT, and G418 as a selection marker. The tricistronic vector was engineered from the pQCXIN backbone containing hTERT. The immortalization process was based on previously published protocols with some modification (Ramirez et al., 2004, Cancer Res 64:9027; Sato et al., 2006, Cancer Res 66:2116). The gBECs and gSACs have a diploid karyotype and are non-tumorigenic.

Tumor Samples:

DNA methylation assays were performed on tumor DNA isolated from FFPE biopsy material obtained from patients enrolled in TRIBUTE, a phase III trial sponsored by Genentech to compare the survival of 1,079 stage IIIB or stage IV NSCLC patients who received Erlotinib administered concurrently with a regimen of carboplatin and paclitaxel (n=539) to patients who received carboplatin and paclitaxel alone (n=540) (Yauch et al., 2005, Clin Cancer Res 11:8686). DNA was available for 343 TRIBUTE patients and 112 MetMAb patients.

Demethylation of Genomic DNA:

Cells to used for negative controls in the methylation assays were grown in RPMI 1640 supplemented with 10% fetal bovine serum and 2 mM L-Glutamine. Cells were seeded on day 0 at 4000-9000 cells/cm2 and dosed with 1 µM 5-aza-2'-deoxycytidine (SIGMA-ALDRICH Cat No. A3656) or DMSO control (Cat No. D2650) on days 1, 3, and 5. On day 6 cells were washed once in cold Phosphate Buffered Saline and harvested by scraping in Trizol (Invitrogen, Cat No 15596018) and extracted for RNA or flash frozen for later RNA extraction.

Illumina Infinium Methylation Analysis:

1 µg of genomic DNA from each of 96 NSCLC cell lines was bisulfate-converted and analyzed on the Illumina Infinium 450K methylation. Methylation data were processed using the Bioconductor lumi software package (Du et al., 2008, Bioinformatics 24:1547). The Infinium 450K platform includes Infinium I and II assays on the same array. The Infinium I assay employs two bead types per CpG locus, with the methylated state reported by the red dye in some cases and the green dye in others (identical to the previous Infinium 27K platform). The Infinium II assay uses one bead type and always reports the methylated state with the same dye, making dye bias a concern. After discarding one array with high background signal, a two-stage normalization procedure was applied to the remaining arrays. First, for each array, a color-bias correction curve was estimated from Infinium I data using a smooth quantile normalization method; this correction curve was then applied to all data from that array. Second, arrays were normalized to one another by applying standard quantile normalization to all color-corrected signals.

After pre-processing, both methylation M-values ($\log_e$ ratios of methylated to unmethylated probes) and β-values (a rescaling of the M-values to the 0 and 1 range via logistic transform) were computed for each sample (Du et al, 2010, BMC Bioinformatics 11:587). For visualization, agglomerative hierarchical clustering of β-values was performed using complete linkage and Euclidean distance. DMRs were identified by first computing a moving average for each cell line's M-values (500 bp windows centered on interrogated CpG sites); then, a t-test was used to contrast the window scores associated with a training set of randomly selected 10 Epithelial-like and 10 Mesenchymal-like lines. DMR p-values were adjusted to control the False Discovery rate (Benjamini and Hochberg, 1995) and compared to a cutoff of 0.01. To enrich for more biologically relevant phenomena, downstream analyses only considered those differentially methylated regions whose average window scores (i) differed by at least 2 between the sensitive and resistant lines, and (ii) had opposite sign in the two sets of cell lines. Finally, contiguous DMRs which met all of these criteria were merged into a single DMR if they were separated by less than 2 kb.

Bisulfite Sequencing and Analysis:

To confirm DNA methylation status of candidate genes, 2 µg genomic DNA was bisulfate-converted using the EZ DNA Methylation-Gold kit (Zymo Research). Primers specific to the converted DNA were designed using Methyl Primer Express software v1.0 (Applied Biosystems). PCR amplification was performed with 1 µl of bisulfate-converted DNA in a 25-µl reaction using Platinum PCR supermix (Invitrogen). The PCR thermocycling conditions were as follows: 1 initial denaturation cycle of 95° C. for 10 minutes, followed by 10 cycles of 94° C. for 30 seconds, 65° C. for 1 minute and decreasing by 1° C. every cycle, and 72° C. for 1 minute, followed by 30 cycles of 94° C. for 30 seconds, 55° C. for 1.5 minutes, and 72° C. for 1 minute, followed by a final extension at 72° C. for 15 minutes. PCR products were resolved by electrophoresis using 2% agarose E-gels containing ethidium bromide (Invitrogen) and visualized using a FluorChem 8900 camera (Alpha Innotech).

PCR products were ligated into the pCR4-TOPO vector using the TOPO TA Cloning kit (Invitrogen) according to the manufacturer's instructions. 2 µl of ligated plasmid DNA were transformed into TOP10 competent bacteria (Invitrogen), and 100 µl transformed bacteria were plated on LB-agar plates containing 50 µg/ml carbenicillin (Teknova) and incubated overnight at 37° C. Twelve colonies per cell line for each candidate locus were inoculated into 1 ml of LB containing 50 µg/ml carbenicillin and grown overnight in a shaking incubator at 37° C. Plasmid DNA was isolated using a Qiaprep miniprep kit in 96-well format (Qiagen) and sequenced on a 3730×1 DNA Analyzer (Applied Biosystems). Sequencing data were analyzed using Sequencher v4.5 software and BiQ Analyzer software. Bisulfite-converted sequences were first aligned and trimmed to reference sequences for each candidate locus using Sequencher to evaluate sequence quality and confirm cytosine conversion during sodium bisulfite treatment. Trimmed sequences were then evaluated for methylation status at individual CpG sites using BiQ Analyzer software.

Pyrosequencing:

Bisulfite-specific PCR (BSP) primers were designed using Methyl Primer Express software v1.0 (Applied Biosystems) or PyroMark Assay Design software v2.0 (Qiagen). PCR primers were synthesized with a 5' biotin label on either the forward or reverse primer to facilitate binding of the PCR product to Streptavidin Sepharose beads. Sequencing primers were designed in the reverse direction of the 5'-biotin-labeled PCR primer using PyroMark Assay Design software v2.0 (Qiagen). 1 µl bisulfite modified DNA was amplified in a 25 µl reaction using Platinum PCR Supermix (Invitrogen) and 20 µl of PCR product was used for sequencing on the Pyromark Q24 (Qiagen). PCR products were incubated with Streptavidin Sepharose beads for 10 minutes followed by washes with 70% ethanol, Pyromark denaturation solution, and Pyromark wash buffer. Denatured PCR products were then sequenced using 0.3 µM sequencing primer. Pyrograms were visualized and evaluated for sequence quality, and percent methylation at individual CpG sites was determined using PyroMark software version 2.0.4 (Qiagen). The following primers are exemplary primers used in the ERBB2 pyrosequencing assays:

```
ERBB2 Pyrosequencing Primers:
1 Forward:
                              (SEQ ID NO: 3)
5'-GGTTTAAGTGGGTTAGGTGTG-3'

1 Reverse, biotin:
                              (SEQ ID NO: 4)
5'-CAATTATAAACATCTAAACCCAAACTACA-3'

1 Sequencing:
                              (SEQ ID NO: 5)
5'-AGT TTTATGTTTTATGGT TGA-3'

Nested Forward:
                              (SEQ ID NO: 6)
5'-TAGTTTTATGTTTTATGGTTGATGGTT-3'

Nested Reverse, biotin:
                              (SEQ ID NO: 7)
5'-CCAAAACCAACTAACAAAATATATACC-3'

Nested Sequencing:
                              (SEQ ID NO: 8)
5'-TTGGGTAGGTATGTAGG-3'
```

Promoter Enhancer Activity Luciferase Reporter Assay:

Promoter enhancer activity of a differentially methylated region (identified by Infinium array profiling) of the ERBB2 gene was assessed using Dual-Luciferase Reporter Assay System (Promega). A 1791-bp region within the first intron of ERBB2 was cloned into the pGL4 luciferase reporter vector according to the manufacturer's instructions. Cells were transfected with the control promoter plus ERBB2 putative enhancer region, and luciferase activity was measured using a standard luminometer at 24, 48, and 72 hour time points following transfection.

Quantitative Methylation Specific PCR:

Quantitative methylation specific PCR (qMSP) assays were designed using genetic loci identified in our candidate screen as differentially methylated in erlotinib-sensitive and resistant NSCLC cell lines. A minimum of 10 ng of sodium bisulfite converted DNA was amplified with various 20× Custom Taqman Gene Expression Assays, Applied Biosystems, Cat No. 4331348) using TaqMan® Universal PCR Master Mix, No AmpErase® UNG (Applied Biosystems, Cat No. 4324018) with cycling conditions of 95° C. 10 min, then 50 cycles of 95° C. for 15 sec and 60° C. for 1 min. Amplification was done on a 7900HT system and analyzed using SDS software (Applied Biosystems). DNA content was normalized using meRNaseP Taqman assay.

Pre-amplification of FFPE Clinical Trial Material: A pre-amplification method for methylation analysis of pg amounts of DNA extracted from formalin-fixed paraffin embedded (FFPE) tissue was developed. 2 µl (equivalent of 10 pg-1 ng) bisulfite converted DNA was first amplified in a 20 µl reaction with 0.1× qMSP primer-probe concentrations using TaqMan® Universal PCR Master Mix, No AmpErase® UNG (Applied Biosystems, Cat No. 4324018) and cycling conditions of 95° C. 10 min, then 14 cycles of 95° C. for 15 sec and 60° C. for 1 min. 1 µl of the pre-amplified material was then amplified in a second PCR reaction with cycling conditions of 95° C. 10 min, then 50 cycles of 95° C. for 15 sec and 60° C. for 1 min. DNA content was confirmed using a pre-amplification with the reference meRNaseP Taqman assay and only samples that were positive for meRNaseP were included in further analysis of qMSP reactions. All reactions were performed in duplicate.

Example 2—Hypomethylation of the ERBB2 DMR Correlates with an Epithelial-Like Phenotype in NSCLC Cell Lines and in NSCLC Primary Tumors A CpG site near exon 4 of the ERBB2 proto-oncogene was identified as a differentially methylated region (DMR), based on methylation profiling of epithelial and meschenchymal-like NSCLC cell lines. Methylation profiling was performed using Infinium Methylation Analysis, and verification of the methylation status was verified by direct sequencing of cloned fragments of sodium bisulfite-converted DNA.

Pyrosequencing was used to determine quantitative methylation status of the DMR in NSCLC primary tumors and matched normal tissues. Quantitative methylation was determined at 6 consecutive CpG sites by Pyromark analysis software using the equation % methylation=(C peak height× 100/C peak height+T peak height, FIG. 2 (showing the mean percent methylation of 6 individual CpG sites, with a P-value $p<0.06$ determined using a Student's t-test). As shown in FIG. 2, this intragenic DMR of ERBB2 appeared to be hypomethylated relative to normal adjacent tissue.

Figure 3:
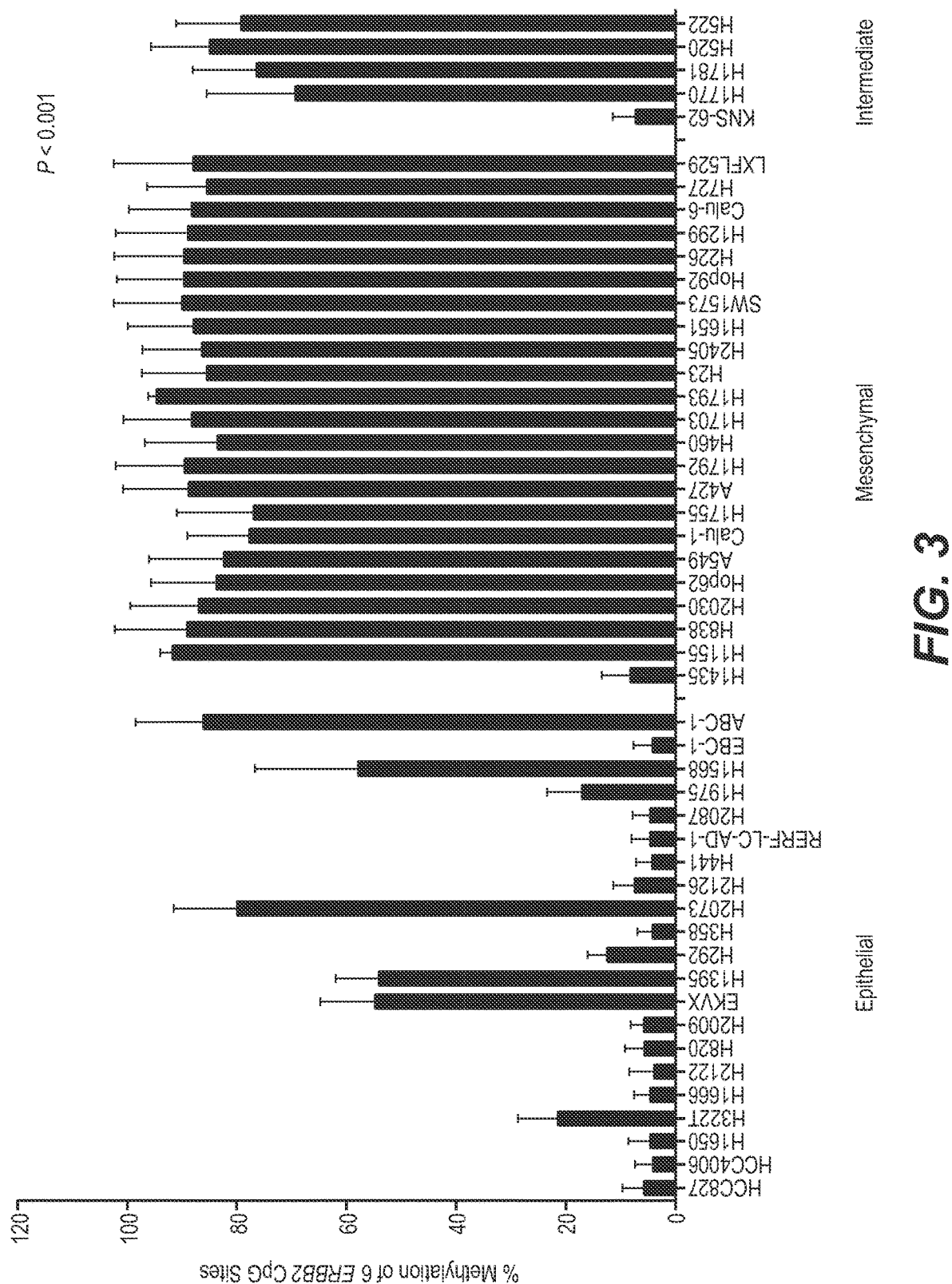
FIG. 3 is a graph depicting the results of a quantitative pyrosequencing analysis of ERBB2 methylation status in epithelial-like and mesenchymal-like NSCLC cell lines.

In silico analysis of this region using the UCSC genome browser suggested that the differentially methylated CpG site corresponding to probe cg00459816 (Type II Illumina Infinium 450K methylation array probe, representing a single CpG site at chromosomal coordinates: NCBI build 36/hg18 chr17:35115639 (Illumina, Inc., San Diego, Calif.) overlapped with a potential regulatory element. Because this region was not within a CpG island and was not particularly GC rich, pyrosequencing primers flanking this region were designed to determine its methylation status in a panel of epithelial-like and mesenchymal-like cell lines. A pattern of hypomethylation (mean methylation of 6 CpG sites ≤20%) in 13 of 16 epithelial-like lines relative to mesenchymal-like lines (mean methylation ≥70% in 20 of 21 mesenchymal-like lines; $P<0.001$) was observed. FIG. 3 shows the results of this analysis, with data being represented as mean+/−SD percentage of methylation at 6 consecutive CpG sites in the sequenced region.

Only one mesenchymal-like line, H1435, was hypomethylated at this locus. This exception was not surprising given our previous observation that H1435 was identified as a mesenchymal-like line by EMT expression analysis.

Example 3—Hypomethylation of the ERBB2 DMR Correlates with ERBB2 Expression

Figure 4:
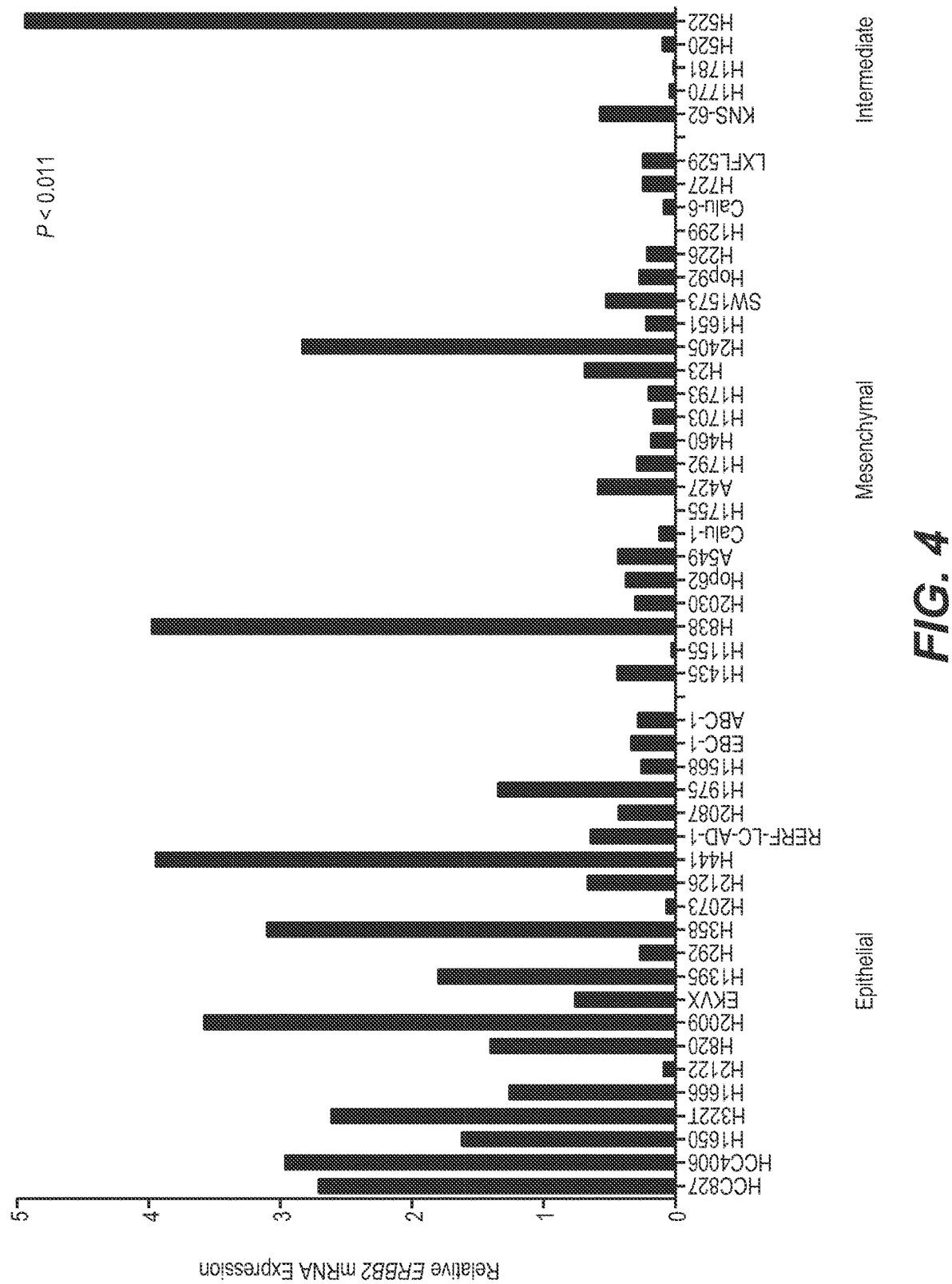
FIG. 4 is a graph showing the relative expression of ERBB2 mRNA in NSCLC cells using TaqMan based Fludigm gene expression analysis.

The relative expression level of ERBB2 mRNA in the NSCLC cell lines was determined using TaqMan-based Fluidigm gene expression analysis. As shown in FIG. 4, epithelial-like lines exhibited significantly higher levels of ERBB2 expression (P<0.001) than mesenchymal-like lines. The finding that hypomethylation of the ERBB2 locus is highly correlated with both higher expression of HER2 in cell lines and with an epithelial phenotype indicates that differential methylation of this region could serve as a predictive biomarker for inhibitors of EGFR or HER2 signaling.

Figure 5:
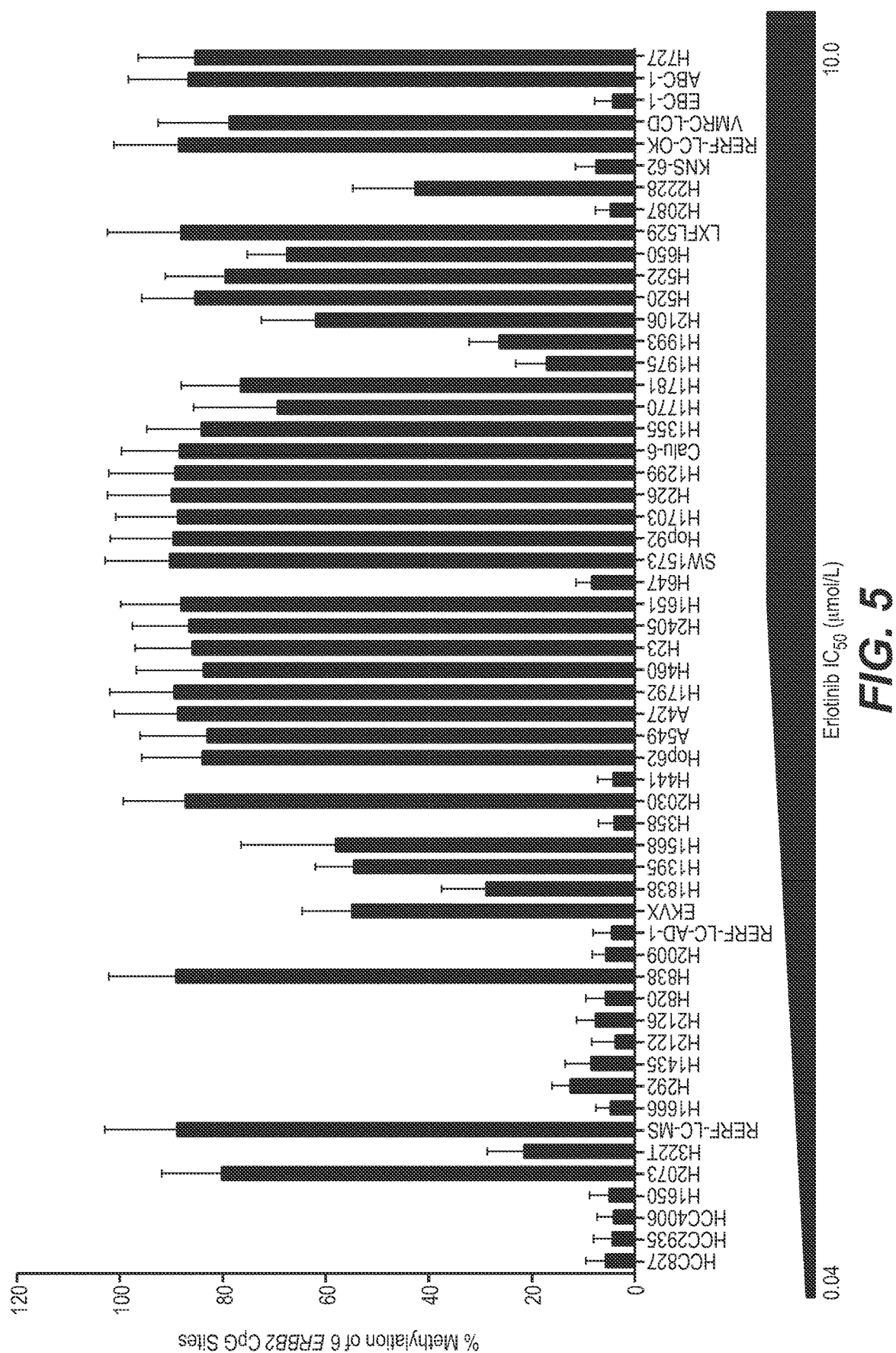
FIG. 5 is a graph depicting percent methylation of ERBB2 enhancer CpG sites in cells lines. The cells lines are ordered by sensitivity to erlotinib treatment.

Example 4—Hypomethylation of the ERBB2 DMR Correlates with Erlotinib Sensitivity ERBB2 hypomethylation was strongly correlated with erlotinib sensitivity in vitro, indicating its potential as a predictive clinical biomarker of erlotinib response. FIG. 5 shows the results of a ERBB2 pyrosequencing analysis of NSCLC cell lines indicating this correlation between ERBB2 hypomethylation and erlotinib sensitivity. Data in this FIG. 5 is plotted as the mean+/−SD of methylation of 6 CpG sites against erlotinib sensitivity. For erlotinib $IC_{50}$ determination, cells were plated in quadruplicate at $3\times10^2$ cells per well in 384-well plates in RPMI containing 0.5% FBS (assay medium) and incubated overnight. 24 hours later, cells were treated with assay medium containing 3 nM TGFα and erlotinib at a dose range of 10 μM-1 pM final concentration. After 72 hrs, cell viability was measured using the Celltiter-Glo Luminescent Cell Viability Assay (Promega). The concentration of erlotinib resulting in the 50% inhibition of cell viability was calculated from a 4-parameter curve analysis and was determined from a minimum of 2 experiments.

Figure 6:
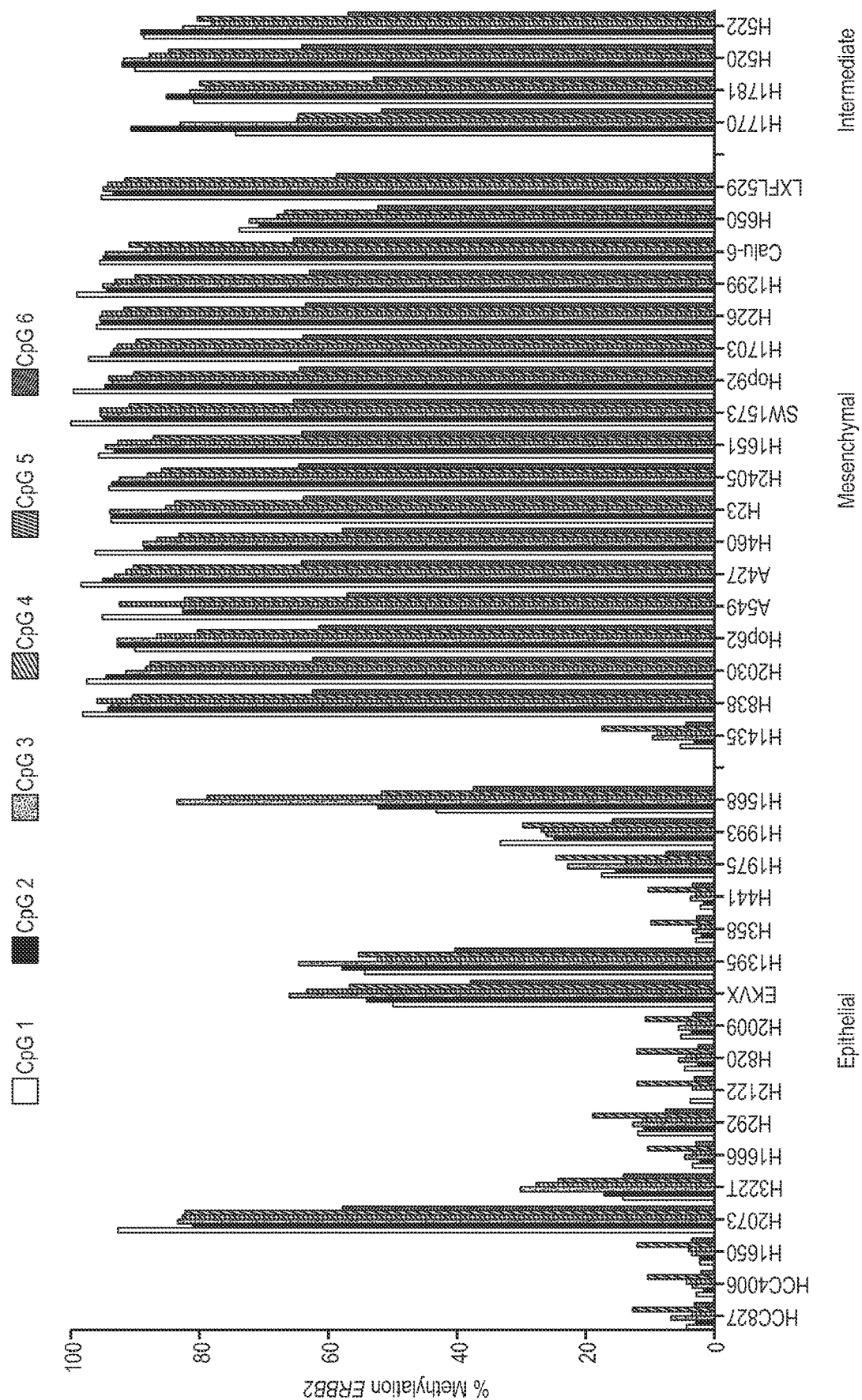
FIG. 6 is a graph depicting the results of a pyrosequencing analysis showing percentages of methylation at each of 6 individual CpG sites in NSCLC surgically resected primary tumors and matched normal tissue.

Example 5—Hypomethylation of the ERBB2 DMR Correlates to an Epithelial-Like Phenotype FFPE Tissue Samples Fresh-frozen samples are not typically obtained during diagnosis of NSCLCs or as part of lung cancer clinical trials. Therefore, to be amenable to clinical applications, a pyrosequencing assay must be able to amplify limited, degraded DNA from formalin-fixed, paraffin-embedded (FFPE) tissue (commonly <150 bp). Because of the high concordance between the methylation states of 6 adjacent CpG sites within the ERBB2 DMR using a 228-bp pyrosequencing assay (FIG. 6), the assay was redesigned to examine just 2 CpG sites. In this assay, pyrosequencing was used to determine quantitative methylation status of the DMR in NSCLC cell lines. Quantitative methylation was determined at 6 consecutive CpG sites by Pyromark analysis software using the equation % methylation=(C peak height×100/C peak height+T peak height). FIG. 6 shows the mean percent methylation of 6 individual CpG sites, with a P-value of p<0.06 determined using a Student's t-test. The designation of the cell lines as epithelial or mesenchymal was previously determined using a 20-gene Fluidigm Gene Expression panel.

Figure 7:
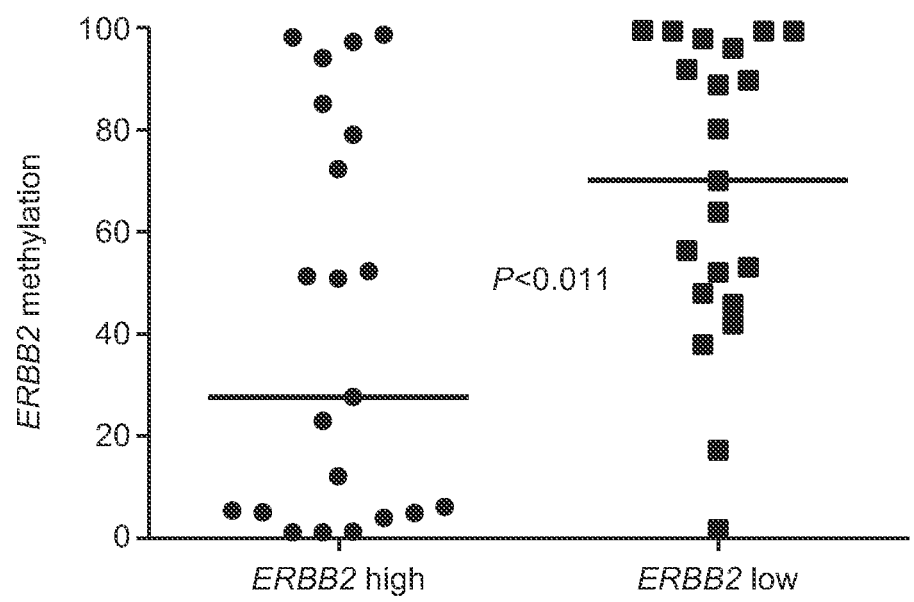
FIG. 7 is a graph depicting percent methylation of ERBB2 enhancer region in high and low ERBB2-expression tumor cells.

Example 6—Hypomethylation of the ERBB2 DMR Correlates with an Epithelial-Like Phenotype in NSCLC Primary Tumors The methylation status of ERBB2 was then evaluated in 42 late-stage (stage IIIb/IV) FFPE NSCLC tumors for which gene expression data were also available. Hypomethylation of the ERBB2 enhancer correlated strongly with expression of HER2 in biopsies obtained from patients who later went on to fail front-line chemotherapy (P<0.011), recapitulating the pattern observed in cell lines (FIG. 7). Hypomethylation was determined using pyrosequencing and TaqMan-based Fluidigm gene express analysis. Percentage of methylation is represented as the mean of 2 CpG sites. A median cutoff point was used to dichotomize ERBB2-high and ERBB2-low tumors. P value was determined using a one-tailed Mann-Whitney U test.

Figure 8:
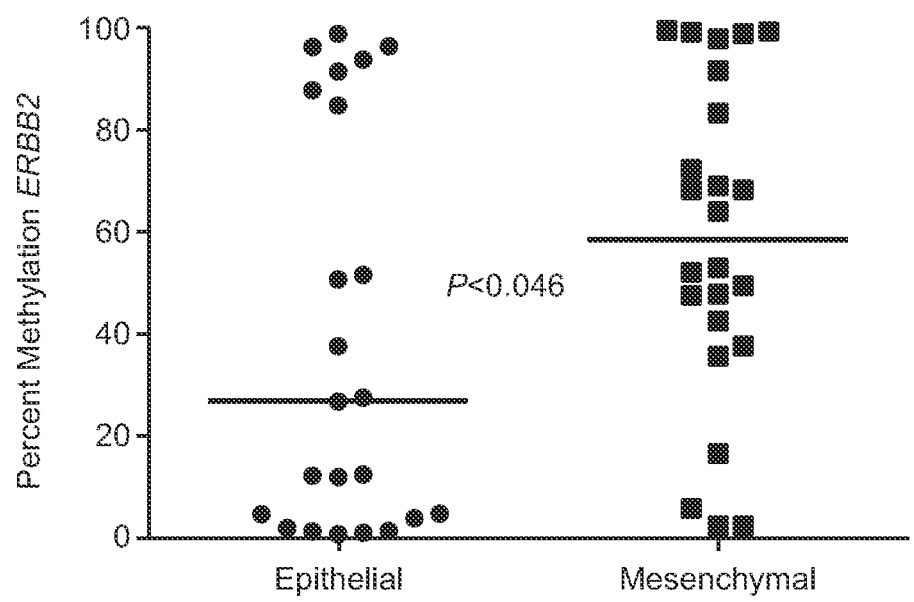
FIG. 8 is a graph depicting pyrosequencing analysis of methylation of ERBB2 and epithelial/mesenchymal status in 47 NSCLC primary tumor samples derived from archival FFPE slides.

Analysis of methylation of ERBB2 and epithelial/mesenchymal status in 47 NSCLC primary tumor samples derived from archival FFPE slides was performed. Methylation status of ERBB2 was determined using pyrosequencing analysis. Tumors that were classified as epithelial-like were hypomethylated at the ERBB2 enhancer relative to tumors classified as mesenchymal-like (P<0.046), indicating a strong association between ERBB2 methylation status and overall gene expression phenotype, FIG. 8 (data are represented as the mean of 2 CpG cites. Epithelial-like/mesenchymal-like status was determined using scores derived from TaqMan-based Fluidigm gene expression analysis. A median cutoff point was used to dichotomize epithelial-like/mesenchymal-like expression scores. P value was determined using a Student t test).

What is claimed is:

1. A method of treating a cancer patient with an EGFR inhibitor comprising the following steps:
   a) detecting the methylation status of the ERBB2 gene from a sample from the patient's cancer;
   b) selecting the cancer patient for the treatment if the methylation status of the ERBB2 gene is detected to be hypomethylation; and
   c) administering an effective amount of the EGFR inhibitor to the cancer patient, wherein the cancer is lung cancer.

2. The method of claim 1, wherein the methylation status is detected in a part of the ERBB2 gene.

3. The method of claim 2, wherein the part of the ERBB2 gene is an enhancer.

4. The method of claim 2, wherein the part of the ERBB2 gene is an enhancer and a promoter.

5. The method of claim 2, wherein the part of the ERBB2 gene comprises a 6 CpG repeat region.

6. The method of claim 5, wherein the part of the ERBB2 gene further comprises the nucleic acid sequence of SEQ ID NO: 2.

7. The method of claim 2, wherein the part of the ERBB2 gene comprises the nucleic acid sequence of SEQ ID NO:1.

8. The method of claim 1, where hypomethylation is indicated by less than about 20% methylation of the ERBB2 gene.

9. The method of claim 1, wherein the EGFR inhibitor is erlotinib, cetuximab or panitumumab.

10. The method of claim 9, wherein the EGFR inhibitor is erlotinib.

11. The method of claim 1, wherein the lung cancer is NSCLC.

12. The method of claim 1, wherein the methylation status is detected by pyrosequencing.

* * * * *

SEQUENCE LISTING

```
<160> NUMBER OF SEQ ID NOS: 8

<210> SEQ ID NO 1
<211> LENGTH: 2551
<212> TYPE: DNA
<213> ORGANISM: Homo sapiens

<400> SEQUENCE: 1
gcccaaccca gcccagccac cctgccctcc gtagagcctg tggtgtttat cggtggcatt      60
gggagaatta gtgtgtattt atgttggcgt ggggtgtggg gtggatttgt gtgtgtgcag     120
```

-continued

| | |
|---|---|
| ttaggcctag tggaaggaat gtgggatctg aaggcaggcc agcctgagtt ccagtcctgc | 180 |
| ctgttgctca caagctttat gaggcgagag ctaacccctg ccagcctcag ttgtcttctt | 240 |
| tgcaagatgg aggttgcagc cccagtctct ggagcatgtt atgcagatcc accgagagtg | 300 |
| cctgccaggc acacagtagg tgctcagctc agttactgtg gcggccccca ctccccattg | 360 |
| ttgttgtttt cctattgcct ggcggccaca gctggtatcc cttgaaaagg gctacagggg | 420 |
| gtggagtcgg accctgcccc agccctgtgg agacctggg cttgggccag gcctggggt | 480 |
| ctgggcctgc agacagctgt gtctataaag cagctgaagg gctgaggccg ggggaggtcc | 540 |
| tggcagcagg gcgttatttt gggcctggcc tgccacccc agctcctgtt tctcttggga | 600 |
| gtctgttggg ggaggaagtg tggggaagag gaggggtgc aagtgggtga ggcatggagt | 660 |
| ggggaggcct ccctcaggga catggaccct tgagttctat ttctgttcct ccctcctgtt | 720 |
| cctccctctt tgtccttatc tgcctagaga ggtgggaata gaggccattc tgagtatcac | 780 |
| taggagacca ccagtttgtg gccactggcc actgggccag gcaggaacc tgggggcttg | 840 |
| ccctaccagc ctctcccagc aatctgaagg caggggtac ctcgtattac ccctaggat | 900 |
| ttgaccttag gctccaactt gctgggagag cagtgcctct ggtgtcagac cccaagccag | 960 |
| cccttgtgct gtccctgaat ctgcatgtag cctgtgggag gcggagcagt gaccggcagg | 1020 |
| aattctgggc agctcaggca cctgtgggcc tgagggtgcc ctctgccccc acccttccga | 1080 |
| tctcctgggc aagacacgcc aggtgattca tctcaccaga gcagaaaaac aagttcaact | 1140 |
| gggcacttta atctcccctc actggcaggc ctggtgtgag ctgctacccc ggcgcccctc | 1200 |
| accagggtg ctttacctcc tctagtattc ctgaccttag tgggcatttc tggtctcagg | 1260 |
| gataccaggc tggggtccaa gtgggccagg tgtggcagtt cagccctatg ccccatggct | 1320 |
| gatggctcgc gctgggcagg tatgcagggc tgacgtagtg cctttgtggc agcagtttcg | 1380 |
| tggcacacat tctgccagct ggttctggag tcttgccctg aggaggtggc cagggtgagg | 1440 |
| gtgccagcgc aggaaccttt ggcgcatgct tcacccctggc ctgggatctg cagcctgggt | 1500 |
| ccagatgccc acaactggaa tctgacgctc cttttctctt catgggggac tcccagaggt | 1560 |
| ctctgcaatg accagagccc cggttgtccc atgcctcagc tgcaactcca gctgaccctc | 1620 |
| cttccccact ctctgggtgg cattacgggg gtgtggatcc cttgccaaga ggttggcatg | 1680 |
| tgggtgtgct ggaatggcat agggagaatg caccgagttt gtttgcttgg gagaggggca | 1740 |
| gggggtatcc agaagattca tgattcgtca tcgcctctct tgggggattt ttaccccttt | 1800 |
| gccctgagtt gtgcctttgg gacaaaggaa gcctttcttt gccagccaac accctgtact | 1860 |
| ggcgggcgag ctccccaggg ctggcacgct ggggcagcct ctgaatgcac agggtgggcc | 1920 |
| tagtcagaag aagcctttcc cctgaaatcc ctctacttcc caagcacgca agctttctcc | 1980 |
| tgctgttaaa cctgcagtgt gcaagggaca tgggcggagg ggtccttcag tcaggcttct | 2040 |
| ccctgtctga ggtggcatga cttggagtga gtttggatgg ggtggccagg tctgagaagg | 2100 |
| tcccccgcca gtgtcctctg acccatctgc tctctcctgc cagtgtgcac cggcacagac | 2160 |
| atgaagctgc ggctccctgc cagtcccgag acccacctgg acatgctccg ccacctctac | 2220 |
| cagggctgcc aggtggtgca gggaaacctg gaactcacct acctgcccac caatgccagc | 2280 |
| ctgtccttcc tgcaggtgag gccgtgggc aacccagcca ggccctgcct ccagctgggc | 2340 |
| tgagccctct gtttacaggt gggtggcaga agaaggtgcc ctgcccttct gtttcctctc | 2400 |
| ttgttgtggt ttctcaacca ggaagtcctt tctaacatct aaccccccatt cattttactg | 2460 |
| cagaatcagt tgactctctc tataacgtgg ctggccgagg tcatgtctgg atgggatgcg | 2520 | tctgtgtttc cgctaaatct tgtgctctct t                                           2551

<210> SEQ ID NO 2
<211> LENGTH: 501
<212> TYPE: DNA
<213> ORGANISM: Homo sapiens

<400> SEQUENCE: 2
tctcagggat accaggctgg ggtccaagtg ggccaggtgt ggcagttcag ccctatgccc     60
catggctgat ggctcgcgct gggcaggtat gcagggctga cgtagtgcct ttgtggcagc    120
agtttcgtgg cacacattct gccagctggt tctggagtct tgccctgagg aggtggccag    180
ggtgagggtg ccagcgcagg aacctttggc gcatgcttca ccctggcctg ggatctgcag    240
cctgggtcca gatgcccaca actggaatct gacgctcctt ttctcttcat ggggactcc     300 cagaggtctc tgcaatgacc agagccccgg ttgtcccatg cctcagctgc aactccagct    360
gaccctcctt ccccactctc tgggtggcat tacggggggtg tggatccctt gccaagaggt   420
tggcatgtgg gtgtgctgga atggcatagg gagaatgcac cgagtttgtt tgcttgggag    480
aggggcaggg ggtatccaga a                                               501

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
ggtttaagtg ggttaggtgt g                                               21

<210> SEQ ID NO 4
<211> LENGTH: 29
<212> TYPE: DNA
<213> ORGANISM: Artificial Sequence
<220> FEATURE:
<223> OTHER INFORMATION: PCR Primer

<400> SEQUENCE: 4
caattataaa catctaaacc caaactaca                                       29

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
agttttatgt tttatggttg a                                               21

<210> SEQ ID NO 6
<211> LENGTH: 27
<212> TYPE: DNA
<213> ORGANISM: Artificial Sequence
<220> FEATURE:
<223> OTHER INFORMATION: PCR Primer

<400> SEQUENCE: 6
tagttttatg ttttatggtt gatggtt                                         27

<210> SEQ ID NO 7

```
<211> LENGTH: 27
<212> TYPE: DNA
<213> ORGANISM: Artificial Sequence
<220> FEATURE:
<223> OTHER INFORMATION: PCR Primer

<400> SEQUENCE: 7
ccaaaaccaa ctaacaaaat atatacc                                               27

<210> SEQ ID NO 8
<211> LENGTH: 17
<212> TYPE: DNA
<213> ORGANISM: Artificial Sequence
<220> FEATURE:
<223> OTHER INFORMATION: PCR Primer

<400> SEQUENCE: 8
ttgggtaggt atgtagg                                                          17
```